United States Patent
Wong et al.

(10) Patent No.: US 6,201,140 B1
(45) Date of Patent: Mar. 13, 2001

(54) 7-0-ETHERS OF TAXANE DERIVATIVES

(75) Inventors: Henry Wong, Durham; Mark D. Wittman, Cheshire, both of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/282,129

(22) Filed: Jul. 28, 1994

(51) Int. Cl.[7] .................. C07D 305/14; A61K 31/337
(52) U.S. Cl. ................. 549/510; 514/449; 514/471; 549/472; 549/473; 549/511
(58) Field of Search .................. 514/449, 471; 549/472, 473, 510, 511

(56) References Cited

U.S. PATENT DOCUMENTS

| | | | |
|---|---|---|---|
| 4,814,870 | 3/1989 | Colin et al. | 514/449 |
| 5,175,315 | 12/1992 | Holton | 549/510 |
| 5,227,400 | 7/1993 | Holton et al. | 514/444 |
| 5,229,526 * | 7/1993 | Holton | 549/213 |

FOREIGN PATENT DOCUMENTS

| | | |
|---|---|---|
| 253738A1 | 1/1988 | (EP) . |
| 534707A1 | 3/1993 | (EP) . |
| 534709A1 | 3/1993 | (EP) . |
| 558959A1 | 9/1993 | (EP) . |
| 590267A2 | 4/1994 | (EP) . |
| 604910A1 | 7/1994 | (EP) . |
| WO93/06079 | 4/1993 | (WO) . |

OTHER PUBLICATIONS

Greene et al, "Protective groups in Organic Synthesis", $2^{nd}$ edition, pp. 10–12, 1991.*

Holton, Robert A., et al, "First Total Synthesis of Taxol. 2. Completion of the C and D Rings", J. AM Chem. Soc., 116, No. 4, p. 1599–1600, 1994.

Kocienski, Philip J., *Protecting Groups*, Chapter 2.4, pp. 42–46, 68–71 and 84, Georg Thieme Verlag Stuttgart, Ed. New York, 1994.

Hepperie, Michael and Georg, Gunda I., "Taxol Analogs", Drugs of the Future, 19 (6), p. 573–584, 1994.

Kingston, David G.I., "Taxol: The Chemistry and Structure–Activity Relationships of a Novel Anticancer Agent," Trends in Biotechnology, 12, No. 6, p. 222–227, Jun., 1994.

Suffness, Matthew, "Taxol: From Discovery to Therapeutic Use," Annual Reports in Medicinal Chemistry, 28, p. 305–314, 1993.

\* cited by examiner

*Primary Examiner*—Ba K. Trinh
(74) *Attorney, Agent, or Firm*—Samuel J. DuBoff; William T. Han

(57) ABSTRACT

The present invention concerns novel 7-ethers of taxane derivatives, their use as antitumor agents and pharmaceutical compositions containing the novel compounds.

23 Claims, No Drawings

7-0-ETHERS OF TAXANE DERIVATIVES

BACKGROUND OF THE INVENTION

1. Field of the Invention

The present invention concerns antitumor compounds. More particularly, the invention provides novel taxane derivatives, pharmaceutical compositions hereof, and their use as antitumor agents.

2. Background Art

Taxol® (paclitaxel) is a natural product extracted from the bark of Pacific yew trees, Taxus brevifolia. It has been shown to have excellent antitumor activity in in vivo animal models, and recent studies have elucidated its unique mode of action, which involves abnormal polymerization of tubulin and disruption of mitosis. It has been recently approved for the treatment of ovarian cancer; and studies involving breast, colon, and lung cancers have shown promising results. The results of paclitaxel clinical studies are reviewed in Rowinsky and Donehower, "The Clinical Pharmacology and Use of Antimicrotubule Agents in Cancer Chemotherapeutics" *Pharmac. Ther.*, 52:35–84, 1991.

Recently, a semi-synthetic analog of paclitaxel named Taxotere® has also been found to have good antitumor activity in animal models. Taxotere® is also currently undergoing clinical trials in Europe and the United States. The structures of paclitaxel and Taxotere® are shown below along with the conventional numbering system of taxane molecules; such numbering system is also employed in this application.

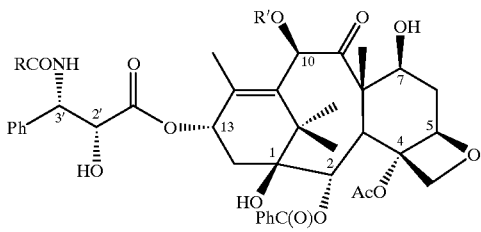

Taxol®: R=Ph; R'=acetyl
Taxotere®: R=t-butoxy; R'=hydrogen

The instant invention relates to a novel class of taxanes. More particularly they are 7-0 ethers of taxane derivatives.

SUMMARY OF THE INVENTION

The present invention relates to taxane derivatives having the formula (I):

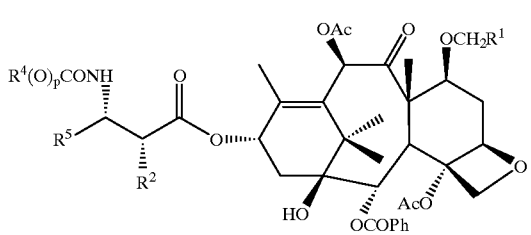

(I)

wherein $R^1$ is hydrogen, $C_{1-8}$ alkyloxy, $C_{2-8}$ alkenyloxy, or $C_{2-8}$ alkynyloxy, each can be optionally substituted with hydroxy; $R^2$ is hydroxy, $—OC(O)R^x$ or $—OC(O)OR^x$; $R^4$ and $R^5$ are independently $C_{1-8}$ alkyl, $C_{2-8}$ alkenyl, $C_{2-8}$ alkynyl, or $—Z—R^6$; p is zero or one; Z is a direct bond, $C_{1-8}$ alkylene or $C_{2-8}$ alkenediyl; $R^6$ is aryl, substituted aryl, $C_{3-8}$ cycloalkyl or heteroaryl; and $R^x$ is $C_{1-8}$ alkyl optionally, substituted with one to six same or different halogen atoms, $C_{3-8}$ cycloalkyl or $C_{2-8}$ alkenyl; or $R^x$ is a radical of the formula

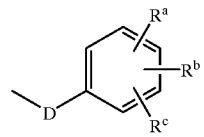

wherein D is a bond or $C_{1-8}$ alkyl; and $R^a$, $R^b$ and $R^c$ are independently hydrogen, amino, $C_{1-8}$ alkylamino, di-$C_{1-8}$ alkylamino, halogen, $C_{1-8}$ alkyl, or $C_{1-8}$ alkyloxy.

Another aspect of the present invention provides a method for inhibiting tumor in a mammalian host which comprises administering to said mammalian host an antitumor effective amount of a compound of the formula (I).

Yet another aspect of the present invention provides a pharmaceutical composition (formulation) which comprises an antitumor effective amount of a compound of the formula (I) and a pharmaceutically acceptable carrier.

DETAILED DESCRIPTION OF THE INVENTION

In the application, unless otherwise specified explicitly or in context, the following definitions apply. "Alkyl" means a straight or branched saturated carbon chain having from one to eight carbon atoms; examples include methyl, ethyl, n-propyl, isopropyl, n-butyl, sec-butyl, isobutyl, t-butyl, n-pentyl, sec-pentyl, isopentyl, n-hexyl, n-heptyl, and n-octyl. "Alkylene" means alkyl with two points of attachment; examples include methylene, ethylene, and propylene. "Alkenyl" means a straight or branched carbon chain having at least one carbon—carbon double bond, and having from two to eight carbon atoms; examples include ethenyl, propenyl, isopropenyl, butenyl, isobutenyl, pentenyl, and hexenyl. "Alkenediyl" refers to alkenyl with two points of attachment; examples include ethylene-1,2-diyl (vinylene), 2-methyl-2-butene-1,4-dinyl, 2-hexene-1,6-diyl, and the like groups. "Alkynyl" means a straight or branched carbon chain having at least one carbon—carbon triple bond, and from two to eight carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl substituted with at least one group selected from $C_{1-8}$ alkanoyloxy, hydroxy, halogen, $C_{1-8}$ alkyl, trifluoromethyl, $C_{1-8}$ alkoxy (alkyloxy), aryl, $C_{2-8}$ alkenyl, $C_{1-8}$ alkanoyl, nitro, amino, and amido. "Halogen" means fluorine, chlorine, bromine, and iodine.

"Methylthiomethyl" (also abbreviated as MTM) refers to the group $—CH_2SCH_3$.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis*, 2d Ed., 1991, John Wiley & Sons, and McOmie, *Protective Groups in Organic Chemistry*, 1975, Plenum Press. Methods for introducing and removing protecting groups are also found in such textbooks.

"Taxane" denotes moieties containing the twenty carbon taxane core framework represented by the structural formula shown below with the absolute configuration.

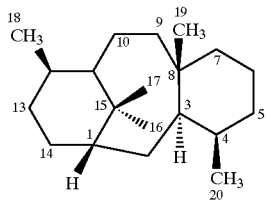

The numbering system shown above is one used in conventional taxane nomenclature, and is followed throughout the application. For example, the notation C1 refers to the carbon atom labelled as "1"; C5–C20 oxetane refers to an oxetane ring formed by the carbon atoms labelled as 4, 5 and 20 with an oxygen atom.

A compound of formula (I) can be prepared by a process of Scheme I. In Scheme I, 7-O-methylthiomethyl is either (1) reduced to 7-O-methyl with Raney Nickel; or (2) reacted with $R^3OH$, in which $R^3$ is $C_{1-8}$ alkyloxy, $C_{2-8}$ alkenyloxy or $C_{2-8}$ alkynyloxy, each can optionally be substituted with hydroxy, in the presence of NIS with triflate as a catalyst. Preferred triflate is silver triflate or trialkylsilyltriflate. An analogous reaction of an alcohol with methylthiomethyloxy group in the presence of NIS was reported by Veeneman et al, in *Tetrahedron*, 1991, v47, pp. 1547–1562, the relevant portions thereof are hereby incorporated by reference.

SCHEME 1

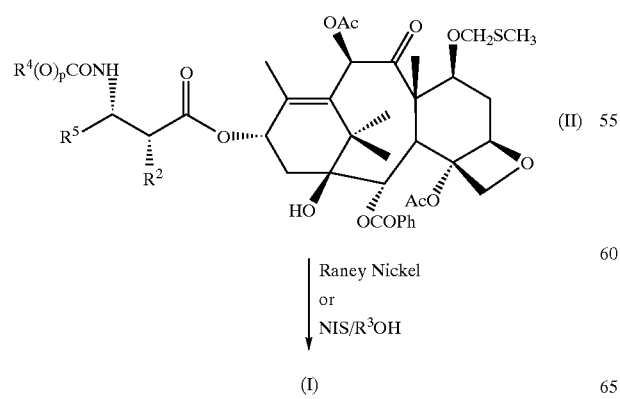

SCHEME IIa

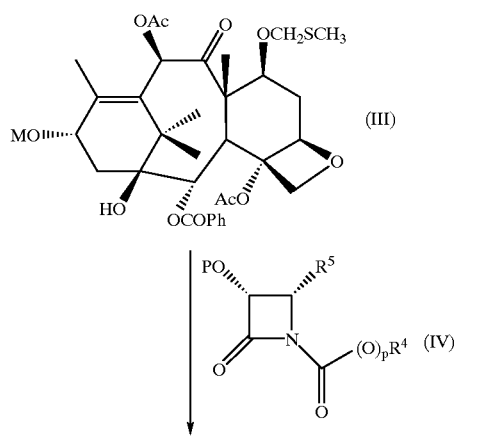

SCHEME IIb

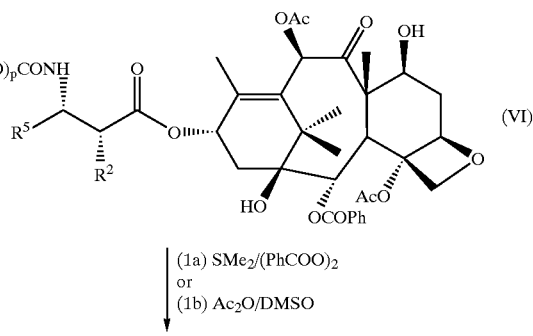

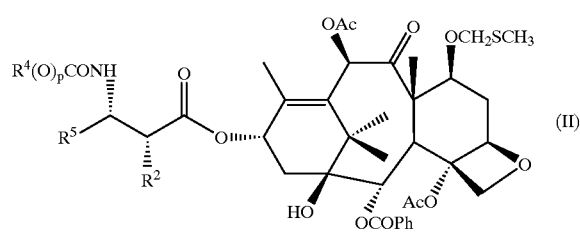

A starting compound of formula (II) can be readily available by either process of Scheme IIa or IIb.

Scheme IIa depicts essentially a coupling as described in EP Application 400,971 published Dec. 5, 1990 (now U.S. Pat. No. 5,175,315) and U.S. Pat. No. 5,229,526. To summarize, the process as disclosed in EP 400,971 (the Holton process) involves reacting 1-benzoyl-3-(1-ethoxy)

ethoxy-4-phenyl-2-azetidinone with 7-O-triethylsilylbaccatin III in the presence of N,N-dimethylaminopyridine and pyridine at 25° C. for 12 hours; paclitaxel is obtained after the various hydroxy protecting groups are removed. An improvement of the Holton process is reported by Ojima et al in "New and Efficient Approaches to the Semisynthesis of Taxol and its C-13 Side Chain Analogs by Means of β-Lactam Synthon Method" Tetrahedron, 1992, 48(34):6985–7012. Ojimals process involves first generating the sodium salt of 7-O-triethylsilylbaccatin III with sodium hydride; this salt is then reacted with chiral 1-benzoyl-3-(1-ethyoxy)ethoxy-4-phenyl-2-azetidinone to provide paclitaxel after removal of the hydroxy protecting groups. In U.S. Pat. No. 5,229,526, Holton discloses the coupling of a metal alkoxide of baccatin III or a derivative thereof with a 2-azetidinone to provide taxanes with C13 sidechain. This process is said to be highly diastereoselective; therefore racemic mixtures of the sidechain precursor 2-azetidinone may be used. Recently, Ojima et al reported in "A Highly Efficient Route to Taxotere by the β-Lactam Synthon Method," Tetrahedron Letters, 1993, 34(26):4149–4152, the coupling of metal alkoxides of 7,10-bis-O-(trichloroethoxycarbonyl)-10-deacetylbaccatin III with chiral 1-(t-butoxycarbonyl)-4-phenyl-3-(protected hydroxy)-2-azetidinone to give Taxotere® after deprotection. The relevant portions of all references cited above are hereby incorporated by reference.

More specifically, in Scheme IIa, P is a hydroxy protecting group; M is hydrogen or a Group IA metal such as lithium, sodium or potassium. The reaction may be conducted according to the procedure disclosed in EP 400,971 wherein the baccatin III derivative of formula (III) wherein M is hydrogen is reacted with an azetidinone of formula (IV) in the presence of an organic base such as N,N-dimethylaminopyridine. Preferably, however, the baccatin III derivative is first converted to a 13-alkoxide by treating the former with a strong base such as hydrides, alkylamides, and bis(trialkylsilyl)amides of Group IA metals as disclosed in U.S. Pat. No. 5,229,526 and the Ojima references, supra. More preferably, the 13-alkoxide is a lithium alkoxide. The formation of a lithium salt may be achieved by reacting a compound of formula (III) wherein M is hydrogen with a strong metal base, such as lithium diisopropylamide, $C_{1-6}$ alkyllithium, lithium bis(trimethylsilyl)amide, phenyllithium, lithium hydride, or the like base.

The coupling reaction between a taxane of formula (III) and an azetidinone of formula (IV) is conducted in an inert organic solvent such as tetrahydrofuran at reduced temperature in the range of about 0° C. to about −78° C. The azetidinones of formula (IV) may be used as a racemic mixture; in such case, the azetidinone reactant is preferably used in at least 2 equivalents relative to the taxane reactant, and more preferably from about 3 to about 6 equivalents. Chiral azetidinones may also be used, and in such case one equivalent of the azetidinone relative to the taxane may be sufficient, but preferably the azetidinone is used in slight excess, for example up to 1.5 equivalents.

After the coupling reaction with a taxane, the hydroxy protecting group P is removed, and if desired, the free hydroxy group on the sidechain may be derivatized to an ester or a carbonate as herein described.

The 2'-hydroxy group of paclitaxel derivatives may be converted by conventional methods to the corresponding ester or carbonate; for example 2'-hydroxy may be reacted with a compound of the formula L—C(O)OR$^x$ (L being a leaving group) such as a chloroformate in the presence of a base such as tertiary amine to give the corresponding carbonate; for example, 2'-hydroxy reacts with ethyl chloroformate in the presence of diisopropylethylamine to provide 2-O-ethyloxycarbonyl derivative. The 2'-hydroxy may also react with a carboxylic acid $RXCO_2H$ or an acylating equivalent thereof (e.g. an anhydride, active ester or an acyl halide) to provide the corresponding ester.

It is to be understood that in Scheme IIa, as well as elsewhere in the specification, hydroxy protecting group may encompass suitable carbonates (e.g. —OC(O)OR$^x$); thus, when a carbonate is used as a hydroxy protecting group, it is intended to be removed in a later step to generate the free hydroxy group; otherwise, the carbonate moiety remains as part of the final product.

Compounds of formula (IV) can be prepared from a compound of (IVa) according to the general method described in EP 400,971 and Ojima et al, Tetrahedron, 48:6985–7012, 1992.

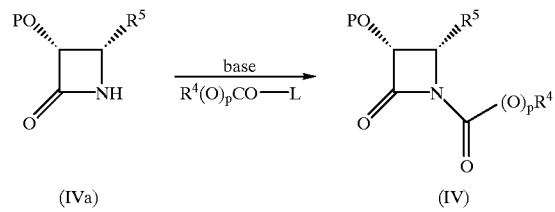

Thus a compound of formula (IVa) is first treated with a base such as n-butyllithium or triethylamine, and then followed by a compound of the formula $R^4(O)_pCO$—L where L is a leaving group to provide a compound of formula (IV).

Compounds of (IVa) may be prepared according to the general method disclosed in EP 400,971 by going through an intermediate compound 3-acetoxy-4-substituted-2-azetidinone (IVb); or by the method disclosed in U.S. Pat. No. 5,229,526 by going through an intermediate compound 3-triethylsilyloxy-4-substituted-2-azetidinone. In an improved process a compound (IVb) may be obtained by condensing acetoxyacetyl chloride with a bis-imine followed by hydrogenolysis or acid cleavage to remove the N-imine group; this process is shown in the following scheme in which $R^{5'}$ is an optionally substituted aryl or a heteroaryl group such as furyl or thienyl. This process is disclosed in co-pending application U.S. Ser. No. 08/165,610 filed Dec. 13, 1993 which is hereby incorporated by reference.

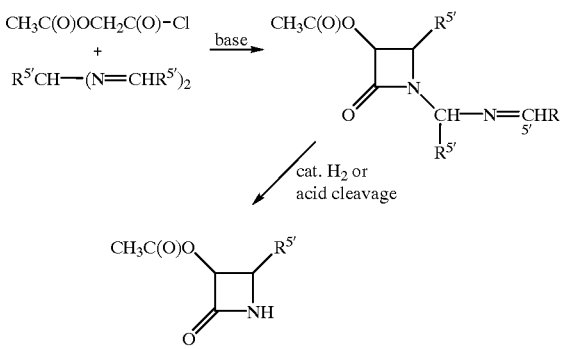

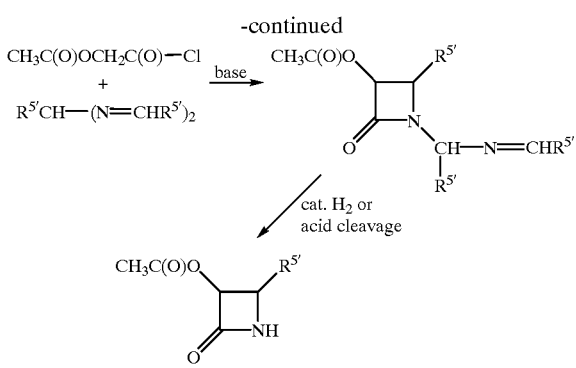

The products (IVb) obtained from these cycloaddition reactions are usually a racemic mixture of the two cis-azetidinones. The racemic mixture may be resolved by conventional methods such as conversion to diastereomers, differential absorption on column packed with chiral adsorbents, or enzymatically. For example, a racemic mixture of compounds of formula (IVb) may be contacted with an enzyme that catalyzes the hydrolysis of an ester, for example an esterase or a lipase, to selectively cleave the 3-acyl group of one enantiomer without affecting the other. (See e.g., Brieva et al, *J. Org. Chem.*, 1993, 58:1068–1075; co-pending application U.S. Ser. No. 092,170 filed Jul. 14, 1993; and European Patent Application Number 552041, published Jul. 21, 1993. These are incorporated herein by reference.). Alternatively, the racemic mixture may be first subjected to base-catalyzed hydrolysis to remove the 3-acyl group and to generate a racemic mixture of the corresponding 3-hydroxy β-lactam; the racemic mixture of 3-hydroxy β-lactam is then contacted with an enzyme capable of catalyzing acylation of an hydroxy group to selectively acylate the hydroxy group of one enantiomer without affecting the other. Or the racemic mixture of 3-hydroxy β-lactam may be acylated with a chiral carboxylic acid, and the resulting diastereomeric mixture may then be separated using methods known in the art, and the chiral auxiliary removed to provide the desired enantiomer.

Ojima et al, in *J. Org. Chem.*, 56:1681–1683, 1991; *Tet. Lett.*, 33:5737–5740, 1992; and *Tetrahedron*, 48:6985–7012, 1992 reported the synthesis of a number of chiral azetidinones of formula (IVa) and/or the corresponding N-(p-methoxyphenyl) congener; wherein P is the hydroxy protecting group triisopropylsilyl; and $R^5$ is 4-methoxyphenyl, 3,4-dimethyoxyphenyl, phenyl, 4-fluorophenyl, 4-trifluoromethylphenyl, 2-furyl, 2-phenylethenyl, 2-(2-furyl)ethenyl, 2-methylpropyl, cyclohexylmethyl, isopropyl, phenethyl, 2-cyclohexylethyl, or n-propyl. Other references for making azetidinones fo formula (IVa) and/or (IV) can be found in European Patent Applications 0,534,709 A1, 0,534,708 A1, and 0,534,707 A1, all three published on Mar. 31, 1993; in PCT application WO 93/06079 published on Apr. 1, 1993; in *Bioorganic and Medicinal Chemistry Letters*, 3, No. 11, pp 2475–2478 (1993); also in *Bioorganic and Medicinal Chemistry Letters*, 3, No. 11, pp 2479–2482 (1993); in *J. org. Chem.*, 58, pp 1068–1075; in *Tetrahedron Letters*, 31, No. 44, pp 6429–6432 (1990); in *Bioorganic and Medicinal Chemistry Letters*, 3, No. 11, pp 2467–2470 (1993); European Application 552,041 published on Jul. 21, 1993; and in our copending U.S. application Ser. No. 092,170 filed on Jul. 14, 1993. The relevant portions of all aforementioned references are hereby incorporated by reference. Other azetidinones within the definition of formula (IV) but are not specifically disclosed in these references may be prepared by a person skilled in the art following the methodologies generally known in the art.

The compounds of formula (II) can also be obtained by a process of Scheme IIb in which one of the two procedures (1a—the dimethylsulfide method) and (1b—the dimethylsulfoxide method) is used. The dimethylsulfide method for converting alcohols to methylthiomethyl ethers is reported in Medina et al, *Tet. Lett.*, 1988, pp. 3773–3776, the relevant portions thereof are hereby incorporated by reference. The dimethylsulfoxide method is the well-known reaction commonly known as the Pummerer reaction.

It should be noted that the reactivity of a hydroxy group differs depending on its location on the taxane derivative starting material of formula (VI). Although in general the 2'-hydroxy group is more reactive in acylation reactions than the 7-hydroxy group, it has been found that, surprisingly with the dimethylsulfide method, the 7-hydroxy is more readily converted into the methylthiomethyl ether than the 2'-hydroxy group. The tertiary hydroxy group at C-1 is usually the least reactive. The difference in hydroxy reactivity may be exploited in controlling the site and degree of methylthiomethylation.

Thus with a compound of formula (VI) wherein $R^2$ is hydroxy, the predominant methylthiomethylation product is the corresponding 7-O-methylthiomethyl ether with the dimethylsulfide method. Even though the 7-hydroxy is the preferential methylthiomethylation site in the dimethylsulfide method, it is still preferable to protect the 2'-hydroxy group; in such case $—OC(O)R^x$ or $—OC(O)R^x$ can serve as protecting group and left as such when $R^2$ in the final desired compound is $—OC(O)R^x$ or $—OC(O)R^x$. Otherwise 2'-hydroxy protecting group is removed from the product.

Returning now to Scheme IIb, in procedure (1a), a compound of formula (VI) is treated with dimethylsulfide and an organic peroxide such as benzoyl peroxide. The reaction is carried out in an inert organic solvent such as acetonitrile, methylene chloride and the like at a temperature conducive to product formation; typically the reaction is carried at a temperature range of from about –40° C. to about ambient temperature. Dimethylsulfide and benzoyl peroxide are used in excess relative to the taxane derivative starting material (VI), and dimethylsulfide is used in excess relative to benzoyl peroxide. Normally, up to 10 fold excess of dimethylsulfide and benzoyl peroxide relative to taxane derivative (VI) is used; and preferably, dimethylsulfide is used in about two to three fold excess relative to benzoyl peroxide.

Alternatively, a compound of formula (II) may be prepared by reacting a compound of formula (VI) with dimethylsulfoxide and acetic anhydride (procedure 1b). In this procedure 2'-hydroxy is preferably protected regardless whether such protecting group is ultimately removed or retained as $—OC(O)R^x$ or $—OC(O)R^x$. In this procedure, a compound of formula (VI) is dissolved in dimethylsulfoxide and acetic anhydride is added to the solution. The reaction is usually carried out at room temperature, and for 18–24 hours to produce the monomethylthiomethyl ether.

The compounds of formula (VI) are well known is the art. For example, they are normally made by reacting appropriately protected baccatin III with azetidinones of formula (IV) as taught in the above discussed U.S. Pat. Nos. 5,175, 315 and 5,229,526; *Tetrahedron*, 1992, 48(34):6985–7012; EP Applications 0,534,709, 0,534,708, and 0,534,707.

Representative In vivo antitumor activity

Balb/c x DBA/2 $F_1$ hybrid mice were implanted intraperitoneally, as described by William Rose in *Evaluation of Madison 109 Lung Carcinoma as a Model for Screening Antitumor Drugs, Cancer Treatment Reports*, 65, No. 3–4 (1981), with 0.5 mL of a 2% (w/v) brei of M109 lung carcinoma.

Mice were treated with compound under study by receiving intraperitoneal injections of various doses on days 5 and 8 post-tumor implant. Mice were followed daily for survival until approximately 75–90 days post-tumor implant. One group of mice per experiment remained untreated and served as the control group.

Median survival times of compound-treated (T) mice were compared to the median survial time of the control (C) mice. The ratio of the two values for each compound-treated group of mice was multiplied by 100 and expressed as a percentage (i.e. % T/C) in Table I for representative compounds of formula (I).

TABLE I

| Example Number | % T/C (mg/kg/inj.) |
| --- | --- |
| 2 | 179 (8) |
| 3 | 118 (5) |
| 5 | 121 (2) |
| 6 | 118 (0.32) |
| 7 | 158 (2) |
| 8 | 208 (8) |
| 9 | 129 (16) |
| 10 | 172 (2) |
| 20 | 118 (16) |
| 21 | 177 (4 or 8) |

Compounds of formula (I) of the instant invention are effective tumor inhibiting agents, and thus are useful in human and/or veterinary medicine. Thus, another aspect of the instant invention concerns a method for inhibiting human and/or other mammalian tumors which comprises administering to a tumor bearing host an antitumor effective amount of a compound of formula (I).

Compounds of formula (I) of the present invention may be used in a manner similar to that of paclitaxel; therefore, an oncologist skilled in the art of cancer treatment will be able to ascertain, without undue experimentation, an appropriate treatment protocol for administering a compound of the present invention. The dosage, mode and schedule of administration for compounds of this invention are not particularly restricted, and will vary with the particular compound employed. Thus a compound of the present invention may be administered via any suitable route of administration, preferably parenterally; the dosage may be, for example, in the range of about 1 to about 100 mg/kg of body weight, or about 20 to about 500 mg/m². The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical compositions (formulations) containing an antitumor effective amount of a compound of formula (I) in combination with one or more pharmaceutically acceptable carriers, excipients, diluents or adjuvants. Examples of formulating paclitaxel or derivatives thereof may be found in, for example, U.S. Pat. Nos. 4,960,790 and 4,814,470, and such examples may be followed to formulate the compounds of this invention. For example, compounds of the present invention may be formulated in the form of tablets, pills, powder mixtures, capsules, injectables, solutions, suppositories, emulsions, dispersions, food premix, and in other suitable forms. They may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are: MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour (s)); NIS (N-iodosuccinimide); BOC (t-butoxycarbonyl); CBZ or Cbz (benzyloxycarbonyl); Bn (benzyl); Bz (benzoyl); TES (triethylsilyl); DMSO (dimethylsulfoxide); THF (tetrahydrofuran); HMDS (hexamethyldisilazane).

Preparation I.

7-O-methylthiomethylpaclitaxel

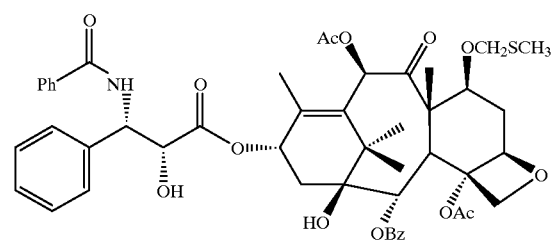

Benzoyl peroxide (0.98 g, 4 mmol) was added to a vigorously stirred mixture of paclitaxel (0.85 g, 1 mmol) and dimethyl sulfide (0.72 mL, 8 mmol) in dry acetonitrile (10 ml) at 0° C. Stirring was continued for 2.5 hours at 0° C. Progress of the reaction was monitored by silica gel TLC in toluene:acetone (2:1, v/v) solvent system ($R_{f\,paclitaxel}$=0.38, $R_{f\,prod.}$=0.64), and when formation of higher polarity products was observed the reaction was quenched by evaporation of solvents using Rotavapor at 30° C. A TLC analysis of the reaction mixture indicated the presence of some quantities of unreacted paclitaxel and 2',7-O-bis(methylthiomethyl) paclitaxel. Separation of the title compound from the reaction mixture was achieved by flash column chromatography on Silica Gel 60 (40–63 μm) EM Science (100 mL), column diameter: 2 in. using ethyl acetate:hexane (1:1, v/v) solvent system ($R_{f\,prod.}$=0.34). The product (552 mg, 60% yield) was recovered from fractions 12 to 18 (each fraction ca. 20 ml).

Preparation II.

7-O-methylthiomethylbaccatin III (7-O-MTM baccatin III)

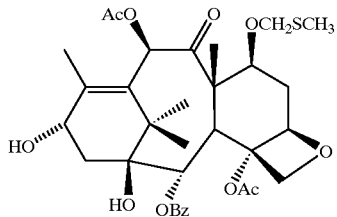

(a) 2'-O-(ethoxycarbonyl)paclitaxel

Paclitaxel (5.40 g, 6.324 mmol) in dry dichloromethane (63 mL) was cooled to 0° C. and treated with neat N,N-diisopropylethylamine (3.30 mL, 3 equiv) and then neat ethyl chloroformate (1.81 mL, 3 equiv) dropwise over a 5 min period. The reaction was monitored by TLC (50% ethyl acetate in hexane). After 2 h at 0° C. and 16 h at room temperature, the reaction was complete and the yellow-orange solution was diluted with ethyl acetate (300 mL) and washed with saturated sodium bicarbonate (3×75 mL) and brine (75 mL). Drying (MgSO₄) and evaporation afforded crude title compound, which was purified by precipitation: dichloromethane (ca. 100 mL) was added followed by cooling and addition of hexane (ca 60 mL) to the cloud point. After cooling in ice for several hours, the solid was collected by filtration. Yield 5.17 g (88%).

(b) 2'-O-(ethoxycarbonyl)-7-O-methylthiomethylpaclitaxel

2'-O-(Ethoxycarbonyl)paclitaxel (2.260 g, 2.4406 mmol) was dissolved in anhydrous dimethylsulfoxide (6 mL), and acetic anhydride (6 mL) was added in one lot at room temperature. The reaction was monitored by HPLC (C18 analytical column; 60% acetonitrile-40% 10 mM ammonium phosphate buffer, pH 6). After 30 h, the solution was diluted with ethyl acetate (250 mL) and washed with saturated aqueous bicarbonate (3 times) then water and brine. After drying over magnesium sulfate and filtration, the crude product was chromatographed on silica (40% ethyl acetate in hexane) to yield the title compound as a white foam (2.030 g, 91%) that was 90% pure by HPLC. A portion was further purified by a second column (5% acetonitrile in dichloromethane) to afford material that was ca. 97% pure by HPLC.

(c) alternate method for the preparation of 2'-O-(ethoxycarbonyl)-7-O-methylthiomethylpaclitaxel 2'-O-(Ethoxycarbonyl)paclitaxel (4.170 g, 4.503 mmol) was dissolved in anhydrous acetonitrile (68 mL) at −40° C., and dimethyl sulfide (3.2 mL, 44.10 mmol) was added, followed by benzoyl peroxide (4.400 g, 18.24 mmol). The mixture was placed in an ice bath and stirred at 0° C., and the course of the reaction was monitored by TLC (40% ethyl acetate in hexane). After 3 h no starting material was detected, and the solution was worked up by adding ethyl acetate (250 mL) and saturated aqueous sodium bicarbonate (100 mL). The organic phase was further washed with bicarbonate, water, and brine, then dried over magnesium sulfate and filtered. The residue was purified by silica gel flash chromatography (4% acetonitrile in dichloromethane), to yield the title compound as a white foam (2.571 g, 58% yield). The purity of this sample was judged as >97% by HPLC.

(d) preparation of 7-O-MTM baccatin III

To a solution of 2'-O-(ethyloxycarbonyl)-7-O-methylthiomethylpaclitaxel (27 g, 27.4 mmol) in 100 mL of THF and 500 mL of methanol was added freshly ground K₂CO₃ (2.7 g, 19 mmol). The solution was stirred for 30 minutes and neutralized with IR-120 (H⁺) resin, filtered and concentrated. The crude filtrate was then dissolved in 200 mL of dichloromethane and stirred for 24 hours with tetrabutylammonium borohydride (10 g). The solution was diluted with dichloromethane and washed with water, saturated bicarbonate and brine. The organic fraction was then dried over MgSO₄ and concentrated. The residue was chromatographed over silica gel (1:1 hexane/ethyl acetate) to give 9.4 g of 7-O-MTM baccatin III (53%) with a melting point of 269° C.

HRFABMS (NOBA) M+H calcd for $C_{33}H_{43}SO_{11}$ 647.2526 Found: 647.2551.

IR (KBr) 3474, 1746, 1724, 1712, 1270, 1240, 1070 cm⁻¹.

¹H NMR (CDCl₃, 300 MHz) δ 8.08 (d, J=7.1 Hz, 2H), 7.58 (t, J=7.5 Hz, 1H), 7.45 (t, J=7.8 Hz, 2H), 6.55 (s, 1H), 4.94 (d, J=8.1 Hz, 1H), 4.83 (br q, J=5.1 Hz, 1H), 4.66 (ABq, J=14.7,12.3 Hz, 2H), 4.30 (m, 2H), 4.13 (d, J=8.4 Hz, 1H), 3.91 (d, J=6.6 Hz, 1H), 2.79 (m, 1H), 2.27 (s, 3H), 2.25 (m, 2H), 2.19 (s, 3H), 2.16 (s, 3H), 2.10 (s, 4H), 1.81 (m, 1H), 1.72 (s, 3H), 1.61 (m, 2H), 1.16 (s, 3H), 1.03 (s, 3H).

¹³C NMR (CDCl₃, 75.5 Hz) δ 202.3, 170.8, 169.3, 167.0, 144.2, 132.6, 132.1, 130.1, 129.4, 128.6, 83.9, 80.9, 78.7, 75.7, 74.5, 73.9, 67.9, 57.6, 47.6, 42.7, 38.3, 26.7, 22.6, 21.0, 20.1, 15.2, 15.0, 10.8.

Preparation III.

3'-N-debenzoyl-3'-N-(t-butyloxycarbonyl)-7-O-methylthiomethylpaclitaxel

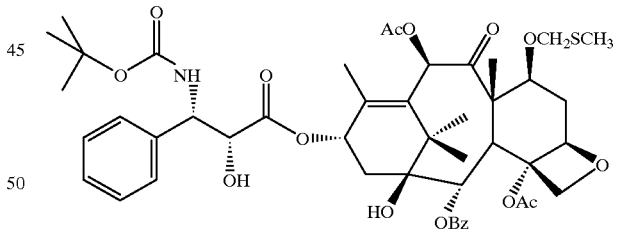

To a solution of hexamethyldisilazane (HMDS) (0.275 mL, 1.30 mmol) in 8 mL of THF was added a solution of n-BuLi (0.48 mL, 2.5 M in hexanes, 1.20 mmol) and stirred 5 minutes at −55° C. To this solution was added 7-O-MTM baccatin III (639 mg, 0.99 mmol) in 8 mL of THF and stirred for 10 minutes before addition of an 8 mL solution of (3R,4S)-1-(t-butyloxycarbonyl)-4-phenyl-3-(triethylsilyloxy)-2-azetidinone (575 mg, 1.52 mmol) in THF. The cold bath was removed and replaced with a 0° C. bath and the reaction stirred for 30 minutes. The solution was diluted with ethyl acetate and washed with saturated NH₄Cl solution, dried over MgSO₄ and concentrated. The residue was chromatographed over silica gel (3:1 hexane/ethyl acetate) to give 1.0 g of the coupling product 3'-N- debenzoyl-3'-N-(t-butyloxycarbonyl)-7-O-methylthiomethyl-2'-O-triethylsilylpaclitaxel (98%).

FABMS (NOBA) M+Na calcd for $C_{52}H_{73}NSSiO_{15}$: 1046. Found: 1046.

IR(film) 3448 (s), 1720, 1242, 1120, 1056 cm$^{-1}$.

$^1$H NMR (CDCl$_3$, 300 MHz) δ 8.09 (d, J=6.9 Hz, 2H), 7.57 (m, 1H), 7.46 (t, J=7.8 Hz, 2H), 7.35 (m, 2H), 7.26 (m, 3H), 6.55 (s, 1H), 6.25 (t, J=9.6 Hz, 1H), 5.68 (d, J=6.9 Hz, 1H), 5.45 (br d, J=9.3 Hz, 1H), 5.27 (br d, 1H), 4.95 (d, J=7.8 Hz, 1H), 4.65 (s, 2H), 4.53 (s, 1H), 4.29 (m, 2H), 4.17 (d, J=8.4 Hz, 1H), 3.89 (d, J=6.9 Hz, 1H), 2.81 (m, 1H), 2.51 (s, 3H), 2.37 (dd, J=15.3, 9.6 Hz, 1H), 2.17 (s, 3H), 2.10 (s, 3H), 2.03 (s, 3H), 1.85 (m, 1H), 1.74 (s, 3H), 1.63 (d, J=14.1 Hz, 1H), 1.29 (s, 9H), 1.21 (s, 6H), 0.76 (t, J=7.8 Hz, 9H), 0.36 (m, 6H).

$^{13}$C NMR (CDCl$_3$, 75.5 Hz) δ 202.0, 171.6, 170.1, 169.3, 167.1, 155.2, 141.0, 139.0, 133.6, 132.8, 130.2, 129.2, 128.7, 128.5, 127.7, 126.4, 83.9, 81.2, 79.9, 78.9, 76.0, 75.7, 75.2, 74.8, 74.2, 71.3, 57.3, 56.7, 47.0, 43.3, 35.3, 33.0, 28.2, 26.4, 23.0, 21.5, 21.0, 15.0, 14.4, 10.9, 6.5, 4.3.

To a solution of the silyl ether obtained above (269 mg, 0.26 mmol) in 6 mL of THF was added tetrabutylammonium fluoride (0.3 mL, 1.0 M in THF, 0.3 mmol) and stirred 10 minutes. The solution was diluted with ethyl acetate and washed with brine, dried over MgSO$_4$ and concentrated and the residue was chromatographed over silica gel (1:1 hexane/ethyl acetate) to give 240 mg of the title compound (95%).

FABMS (NOBA) M+Na calcd for $C_{47}H_{59}NO_{15}SNa$: 932. Found: 932.

IR (film) 3440, 1720, 1370, 1242, 1170, 1108, 1066, 756 cm$^{-1}$.

$^1$H NMR (CDCl$_3$, 300 MHz) δ 8.06 (d, J=7.2 Hz, 2H), 7.57 (t, J=7.2 Hz, 1H), 7.46 (t, J=7.8 Hz, 2H), 7.35 (m, 5H), 6.52 (s, 1H), 6.16 (t, J=8.7 Hz, 1H), 5.64 (d, J=6.9 Hz, 1H), 5.43 (br d, J=9.3 Hz, 1H), 5.24 (br d, J=8.1 Hz, 1H), 4.91 (d, J=8.1 Hz, 1H), 4.63 (m, 3H), 4.26 (m, 2H), 4.14 (d, J=8.4 Hz, 1H), 3.83 (d, J=6.9 Hz, 1H), 3.46 (d, J=5.4 Hz, 1H), 2.77 (m, 1H), 2.34 (s, 3H), 2.27 (m, 1H), 2.16 (s, 3H), 2.09 (s, 3H), 1.97 (s, 3H), 1.79 (m, 2H), 1.72 (s, 3H), 1.32 (s, 9H), 1.19 (s, 3H), 1.18 (s, 3H).

$^{13}$C NMR (CDCl$_3$, 75.5 Hz) δ 202.0, 172.7, 170.3, 169.2, 167.0, 155.3, 140.3, 138.4, 133.7, 133.2, 130.2, 129.1, 128.8, 128.7, 128.0, 126.7, 83.9, 81.3, 80.2, 78.6, 76.5, 76.1, 75.4, 74.6, 74.0, 73.6, 72.3, 57.4, 56.1, 47.1, 43.2, 35.3, 32.8, 28.2, 26.5, 22.6, 21.0, 15.1, 14.6, 10.9.

Preparation IV.
3'-N-debenzoyl-3'-desphenyl-3'-N-(t-butyloxycarbonyl)-3'-(2-furyl)-7-O-methylthiomethylpaclitaxel

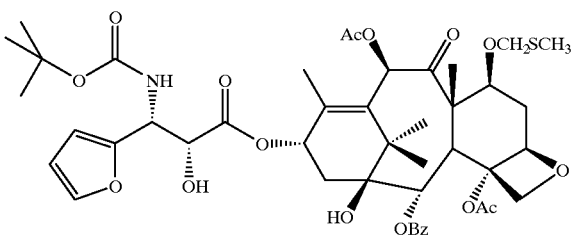

To a solution of HMDS (0.40 mL, 1.90 mmol) in 15 mL of THF was added a solution of n-BuLi (0.75 mL, 2.5 M in hexanes, 1.88 mmol) and stirred 5 minutes at −55° C. To this solution was added 7-O-MTM baccatin III (1.03 g, 1.59 mmol) in 10 mL of THF and stirred for 10 minutes before addition of an 10 mL solution of (2R,3R)-1-(t-butyloxycarbonyl)-4-(2-furyl)-3-(triethylsilyloxy)-2-azetidinone (883 mg, 2.40 mmol) in THF. The cold bath was removed and replaced with a 0° C. bath and the reaction stirred for 30 minutes. The solution was diluted with ethyl acetate and washed with saturated NH$_4$Cl solution, dried over MgSO$_4$ and concentrated. The residue was chromatographed over silica gel (2.5:1 hexane/ethyl acetate) to give 1.5 g of the coupling product 3'-N-debenzoyl-3'-desphenyl-3'-N-(t-butyloxycarbonyl)-3'-(2-furyl)-7-O-methylthiomethyl-2'-O-triethylsilylpaclitaxel (93%).

FABMS (NOBA) M+Na calcd for $C_{50}H_{71}NSSiO_{16}$: 1036. Found: 1036.

IR (film) 3446 (s), 1720, 1368, 1242, 1166, 1144, 1124, 1066 cm$^{-1}$.

$^1$H NMR (CDCl$_3$, 300 MHz) δ 8.07 (d, J=7.2 Hz, 2H), 7.56 (m, 1H), 7.46 (t, J=7.5 Hz, 2H), 7.36 (m, 1H), 6.56 (s, 1H), 6.33 (m, 1H), 6.20 (m, 2H), 5.67 (d, J=6.9 Hz, 1H), 5.29 (br s, 2H), 4.94 (d, J=7.8 Hz, 1H), 4.75 (s, 1H), 4.65 (s, 2H), 4.28 (m, 2H), 4.16 (d, J=8.1 Hz, 1H), 3.89 (d, J=6.9 Hz, 1H), 2.80 (m, 1H), 2.46 (s, 3H), 2.37 (m, 1H), 2.22 (m, 1H), 2.16 (s, 3H), 2.10 (s, 3H), 2.04 (s, 3H), 1.84 (m, 1H), 1.74 (s, 3H), 1.65 (m, 1H), 1.33 (s, 9H), 1.20 (s, 3H), 1.19 (s, 3H), 0.81 (t, J=7.8 Hz, 9H), 0.47 (m, 6H).

$^{13}$C NMR (CDCl$_3$, 75.5 Hz) δ 202.0, 171.2, 170.3, 169.3, 167.1, 155.3, 152.0, 141.9, 141.0, 133.6, 132.9, 130.2, 129.2, 128.7, 110.7, 107.3, 84.0, 81.1, 80.2, 78.7, 76.1, 75.7, 74.7, 74.1, 72.4, 71.1, 57.4, 52.8, 47.1, 43.3, 35.2, 33.0, 28.1, 26.3, 22.9, 21.2, 21.0, 15.0, 14.5, 10.9, 6.5, 4.3.

To a solution of the silyl ether obtained above (330 mg, 0.32 mmol) in 7 mL of THF was added tetrabutylammonium fluoride (0.35 mL, 1.0M in THF, 0.35 mmol) and stirred 10 minutes. The solution was diluted with ethyl acetate and washed with brine, dried over MgSO$_4$ and concentrated and the residue was chromatographed over silica gel (2:1 hexane/ethyl acetate) to give 301 mg of the title compound (95%).

FABMS (NOBA) M+H calcd for $C_{45}H_{58}NO_{16}S$: 900. Found: 900.

IR (film) 3442, 1720, 1242, 1066, 1026 cm$^{-1}$.

$^1$H NMR (CDCl$_3$, 300 MHz) δ 8.07 (d, J=7.3 Hz, 2H), 7.57 (t, J=7.3 Hz, 1H), 7.45 (t, J=7.8 Hz, 2H), 7.38 (s, 1H), 6.53 (s, 1H), 6.34 (d, J=3.2 Hz, 1H), 6.29 (d, J=3.2 Hz, 1H), 6.17 (t, J=8.1 Hz, 1H), 5.65 (d, J=6.9 Hz, 1H), 5.29 (m, 2H), 4.92 (d, J=8.0 Hz, 1H), 4.70 (m, 1H), 4.64 (d, J=4.6 Hz, 2H), 4.29 (m, 2H), 4.14 (d, J=8.3 Hz, 1H), 3.86 (d, J=6.8 Hz, 1H), 3.37 (d, J=5.8 Hz, 1H), 2.77 (m, 1H), 2.38 (s, 3H), 2.32 (m, 2H), 2.16 (s, 3H), 2.10 (s, 3H), 2.02 (s, 3H), 1.75 (m, 6H), 1.33 (s, 9H), 1.17 (s, 3H), 1.12 (s, 3H).

$^{13}$C NMR (CDCl$_3$, 75.5 Hz) δ 202.0, 172.6, 170.3, 169.2, 167.0, 155.2, 151.3, 142.4, 140.4, 133.7, 133.2, 130.2, 129.1, 128.7, 110.7, 107.4, 83.9, 81.2, 80.5, 78.6, 76.5, 76.1, 75.4, 74.6, 74.0, 72.5, 71.8, 57.4, 51.7, 47.2, 43.2, 35.2, 32.8, 28.1, 26.4, 22.6, 20.9, 15.2, 14.6, 10.9, 8.3.

Preparation V.
(3R,4S)-1-t-Butoxycarbonyl-4-phenyl-3-triethylsilyloxy-2-azetidinone

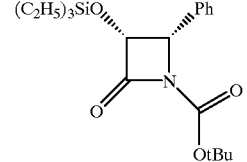

To a stirred solution of (3R,4S)-4-phenyl-3-triethylsilyloxy-2-azetidinone (2.200 g, 7.92 mmol) in dry tetrahydrofuran (25 mL) was added N,N- diisopropylethylamine (1.65 mL. 9.510 mmol, 1.2 equiv) at 0° C. under an argon atmosphere. The solution was stirred for 5 min followed by the addition of di-t-butyl dicarbonate (2.080 g, 9.510 mmol, 1.2 equiv) and 4-dimethylaminopyridine (193.6 mg, 1.581 mmol, 0.20 equiv). The reaction mixture was stirred at 0° C. for 60 min., then diluted with ethyl acetate (25 mL). The resulting solution was washed with brine, 10% NaHCO$_3$, 10% HCl solution, dried (MgSO$_4$), and concentrated to give a crude compound (oil). The compound was further purified by silica gel flash chromatography (being eluted with 15% ethyl acetate in hexanes) to afford the title compound as a white solid (2.4 g, Y: 83%).

Preparation VI.

(±)-cis-3-Acetyloxy-4-phenylazetidin-2-one

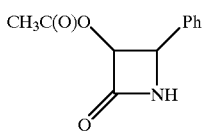

(a) To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxyacetyl chloride (12.4 mL, 116 mmol) in ethyl acetate (300 mL) was then added dropwise over a 90 min period. After 16 h at this temperature, the reaction mixture was allowed to warm to 20° C. (1.5 h) and transferred to a separatory funnel. The organic layer was washed successively with aqueous NH$_4$Cl (sat) (150 mL, 100 mL), aqueous NaHCO$_3$ (saturated) (120 mL) and brine (120 mL). For purposes of characterization, the title compound can be isolated at this stage by drying the organic phase over MgSO$_4$, filtering, and removing the solvent in vacuo. This provided (±)-cis-3-acetyloxy-1-[(phenyl)(benzylidenimino)methyl]-4-phenylazetidin-2-one in quantitative crude yield as a red glass.

(b) A solution of the compound obtained in part (a) in ethyl acetate (500 mL) was carefully transferred, under a stream of argon, to a 2.0 L Parr flask containing 10% palladium on activated charcoal (6.00 g). This mixture was treated with hydrogen (4 atm) for 20 h whereupon the catalyst was removed by filtration through a pad of Celite. The filter cake was slurried in ethyl acetate (200 mL), stirred (10 min) and filtered. The filter cake was rinsed with ethyl acetate (100 mL) and the filtrates combined. The organic layer was washed with 10% HCl (300 mL) and both layers filtered through a sintered glass funnel to remove the white precipitate (dibenzylamine-HCl) which was rinsed with ethyl acetate (100 mL). The phases were separated and the organic layer was washed with another portion of 10% HCl (200 mL). The combined 10% HCl washes were re-extracted with ethyl acetate (200 mL) and the combined organic layers were washed with aqueous NaHCO$_3$ (saturated) (300 mL) and brine (250 mL). The organic layer was dried over MgSO$_4$, filtered and concentrated in vacuo to a final volume of 75 mL. This mixture was cooled to 4° C. and the precipitated product isolated by filtration. The filter cake was washed with hexane (200 mL) to provide 16.12 g (78.1% overall yield from hydrobenzamide) of the title compound as white needles.

mp=150–151° C.

Preparation VII.

(±)-cis-3-Triethylsilyloxy-4-(2-furyl)-N-t-butoxycarbonylazetidin-2-one

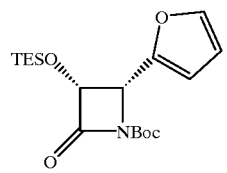

(a) The procedure described in Preparation VI, part (a), was followed except that hydrofuramide [i.e. 2-furyl-CH—(N=CH—2-furyl)$_2$] was used instead of hydrobenzamide and the reaction was performed on 18.6 mmol (vs 100 mmol) scale. Thus, hydrofuramide (5.00 g, 18.6 mmol), triethylamine (3.11 mL, 22.3 mmol) and acetoxyacetyl chloride (2.30 mL, 21.4 mmol) gave 6.192 g (Y: 90.4%) of (±)-cis-3-acetyloxy-1-[(2-furyl)(2-furylmethylenimino)methyl]-4-(2-furyl)azetidin-2-one as a pale red syrup.

(b) The procedure described in Preparation VI, part (b), was followed except that the product was isolated by preparative TLC and the reaction was performed on the 2.7 mmol scale based on the original amount of hydrofuramide. Thus, the crude product obtained in part (a) above was re-dissolved in ethyl acetate (50 mL) and added to 10% palladium on activated charcoal (150 mg). Purification of the crude solid by preparative TLC (2 mm silica gel, eluted with 1:1 ethyl acetate/hexane) gave 386 mg (65.8% corrected overall yield from hydrofuramide) (±)-cis-3-(acetyloxy)-4-(2-furyl)azetidin-2-one as a yellow solid. This was recrystallized from ethyl acetate/hexane.

mp=118–119° C.

(c) The compound obtained in part (b) above (3.78 g, 19.4 mmol) in 60 mL of methanol was stirred with K$_2$CO$_3$ (20 mg, 0.14 mmol) for 90 min and the solution neutralized with Dowex 50W-X8 and filtered. The filtrate was concentrated and the residue dissolved in 80 mL of anhydrous THF and stirred at 0° C. with imidazole (1.44 g, 21.2 mmol) and TESCl (3.4 mL, 20.2 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 4.47 g (Y: 86%) of (±)-cis-3-triethylsilyloxy-4-(2-furyl)-azetidin-2-one as a colorless oil.

(d) The product of part (c) (2.05 g, 7.7 mmol) in 30 mL of dichloromethane was stirred at 0° C. with diisopropylethyl amine (1.5 mL, 8.6 mmol) and di-t-butyl dicarbonate (2.0 g, 9.2 mmol) in addition to a catalytic amount of dimethylaminopyridine (DMAP). The solution was diluted with dichloromethane and washed with brine, dried over MgSO$_4$ and concentrated. The residue was chromatographed over silica gel (eluted with 8:1 hexane/ethyl acetate) to give 2.0 (Y: 70%) of the title compound as a waxy solid.

The racemic mixture obtained in part (b) may be used as substrate for enzymatic hydrolysis using a lipase such as PS-30 from Pseudomonas sp. (Amano International Co.) to give (3R,4R)-3-hydroxy-4-(2-furyl)-azetidin-2-one. The method of enzymatic resolution using the lipase PD-30 and other enzymes is disclosed in our co-pending application U.S. Ser. No. 092,170, filed Jul. 14, 1993 which is hereby incorporated by reference in its entirety.

The general procedure in parts (c) and (d) was followed using (3R,4R)-3-hydroxy-4-(2-furyl)-azetidin-2-one to provide (3R,4R)-N-(t-butoxycarbonyl)-3-triethylsilyoxy-4-(2-furyl)azetidine-2-one.

Preparation VIII.
(±)-cis-3-Triethylsilyloxy-4-(2-thienyl)-N-t-butoxycarbonylazetidin-2-one

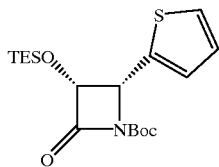

(a) The procedure described in Preparation VI, step (a) was followed except that hydrothienamide [i.e. 2-thienyl-CH═(N═CH─2-thienyl)$_2$] was used instead of hydrobenzamide. Thus, hydrothienamide (30 g, 94.7 mmol), thiethylamine (15.84 mL, 114 mmol) and acetoxyacetyl chloride (11.6 mL, 108 mmol) provided (±)-cis-3-acetyloxy-1-[(2-thienyl)(2-trienylmethylenimino)methyl]-4-(2-thienyl)azetidin-2-one as viscous oil.

(b) A 70% aqueous solution of acetic acid (0.35 mL glacial acetic acid and 0.15 mL water) was added in one portion to a stirred solution of the product obtained in part (a) (.431 g, 1.03 mmol) in dichloromethane (2.93 ml) at 25° C. The reaction mixture was brought to reflux and stirred for 2.5 h. The reaction was diluted with 50 mL dichloromethane and then washed with two 75 mL portions of saturated aqueous sodium bicarbonate and then one 50 mL portion of saturated brine. The organic extract was concentrated in vacuo to a brown oil, dissolved in a minimal amount of dichloromethane, and then placed on a silica gel column measuring 4" by 0.5". Elution using a gradient of 10 through 60% EtOAc in hexane provided less polar sideproducts and then (±)-cis-3-acetyloxy-4-(2-thienyl)azetidin-2-one (0.154 g, Y: 75%) as a white solid.

(c) A solution of the product obtained in part (b) (2.5 g, 11.8 mmol) was dissolved in methanol (10 mL) and treated with saturated aqueous sodium bicarbonate (10 mL) and the resulting slurry was allowed to stir at ambient temperature for 3 h. The reaction was then diluted with ethyl acetate (20 mL) and washed with water (15 mL). The aqueous fraction was back extracted several times with ethyl acetate and the combined organic fractions were dried (MgSO$_4$) and concentrated to give a yellow solid (Y: 1.7 g). The crude material was dissolved in dry tetrahydrofuran (20 mL) and the solution was cooled to 5° C. in an ice/water bath. Imidazole (752 mg, 1.1 eq) was then added. After stirring 5 min, triethylchlorosilane (1.85 mL, 1.1 eq) was added dropwise. The resulting suspension was allowed to stir for 3 h at that temperature; then the solids were removed by filtration. The organic fraction was washed with water (2×20 mL) then dried (MgSO$_4$) and concentrated. The crude product was purified by silica gel column chromatography (eluted with hexanes/ethyl acetate 7:3) to give (±)-cis-3-triethylsilyloxy-4-(2-thienyl)-azetidin-2-one as a colorless solid (1.5 g, Y: 45%). m.p. 70–71° C.

Alternate Run:
The product obtained in part (b) (2.0 g, 9.37 mmol) in 40 mL of methanol was stirred with K$_2$CO$_3$ (60 mg, 0.43 mmol) for 30 min and the solution neutralized with Dowex 50W-X8 and filtered. The filtrate was concentrated and the residue dissolved in 50 mL of anhydrous THF and stirred at 0° C. with imidazole (0.85 g, 11.3 mmol) and TESCl (1.9 mL, 12.5 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 2.13 g (Y: 86%) of the title product as a colorless oil.

(d) A solution of the product obtained in part (c) (425.7 mg, 1.48 mmol) was dissolved in dichloromethane (10 mL) and cooled to 5° C. in an ice/water bath. The reaction was treated with a catalytic amount of DMAP followed by diisopropylethylamine (TESCl, 0.25 mL, 1.0 eq) then by di-t-butyl dicarbonate (388.4 mg, 1.2 eq). After stirring 2 h at that temperature the reaction was quenched with saturated aqueous sodium bicarbonate (5 mL) and the organic fraction was washed with water (5 mL) then dried (MgSO$_4$), passed through a short plug of silica gel and concentrated to give the desired product as a colorless oil (525.3 mg, Y: 93%).

Preparation IX.
(3R,4R)-3-Triethylsilyloxy-4-(2-furyl)-N-n-butyloxycarbonylazetidin-2-one

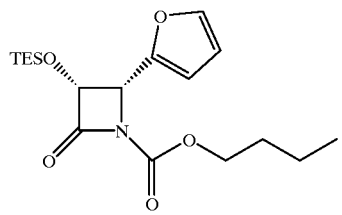

(3R,4R)-3-Triethylsilyloxy-4-(2-furyl)azetidin-2-one (0.58 g, 2.17 mmol) in 30 mL of dichloromethane was stirred with diisopropylethyl amine (0.4 mL, 2.30 mmol) and butylchloroformate (0.3 mL, 2.36 mmol) in addition to a catalytic amount of DMAP. The solution was stirred for 1 h and diluted with dichloromethane and washed with brine, dried over MgSO$_4$ and concentrated. The residue was chromatographed over silica gel (eluted with 3:1 hexane/ethyl acetate) to give 523 mg of product (Y: 65%); IR(KBr) 1820, 1734, 1318, 1018, 734 cm$^{-1}$; 1H-NMR (CDCl$_3$, 300 MHz) δ 7.38 (m, 1H), 6.35 (m, 2H), 5.09 (ABq, J=15.5, 5.6 Hz, 2H), 4.14 (m, 2H), 1.56 (m, 2H), 1.28 (s, 2H), 0.87 (t, J=8.7 Hz, 3H), 0.82 (t, J=7.9, 9H), 0.50 (m, 6H); $^{13}$C-NMR (CDCl$_3$, 75.5 Hz) δ 165.4, 149.1, 147.6, 142.9, 110.5, 109.9, 77.7, 66.6, 55.9, 30.5, 18.8, 13.6, 6.3, 4.3; DCIMS M+H calcd for C$_{18}$H$_{29}$NO$_5$Si: 368, Found: 368.

Preparation X.
(3R,4R)-3-Triethylsilyloxy-4-(2-furyl)-N-isopropyloxycarbonylazetidin-2-one

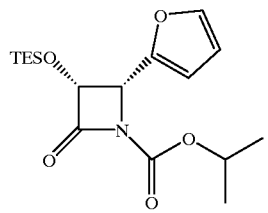

(3R, 4R)-3-Triethylsilyloxy-4-(2-furyl)azetidin-2-one (0.51 g, 1.91 mmol) in 25 mL of dichloromethane was stirred with diisopropylethyl amine (0.78 mL, 4.4 mmol) and i-propylchloroformate (4.0 mL, 1.0M in toluene, 4.0 mmol) in addition to a catalytic amount of DMAP. The solution was stirred for 1 h and diluted with dichloromethane and washed with brine, dried over MgSO$_4$ and concentrated. The residue was chromatographed over silica gel (eluted with 5:1 hexane/ethyl acetate) to give 649 mg of the title product (Y: 96%); IR(KBr) 1822, 1812, 1716, 1374, 1314, 1186, 1018, 1004, 746 cm$^{-1}$; $^1$H-NMR (CDCl$_3$, 300 MHz) δ 7.39 (m, 1H), 6.35 (m, 2H), 5.08 (ABq, J=15.6, 5.6 Hz, 2H), 4.96 (d, J=10.0 Hz, 1H), 1.25 (d, J=6.3 Hz, 3H), 1.17 (d, J=6.3 Hz, 3H)), 0.83 (t, J=7.8, 9H), 0.50 (m, 6H); $^{13}$C-NMR (CDCl$_3$, 75.5 Hz) δ 165.5, 148.6, 147.8, 142.9, 110.5, 109.9, 77.6, 71.1, 55.9, 21.7, 21.6, 6.3, 4.4; DCIMS M+H calcd for C$_{17}$H$_{28}$NO$_5$Si: 354, Found: 354.

Preparation XI.

(±)-cis-3-Triethylsilyloxy-4-isobutenyl-N-t-butoxycarbonylazetidin-2-one (a) preparation of N-4-methoxy-N-(3-methyl-2-butenyl) benzenamine

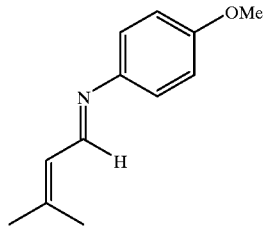

A solution of p-anisidine (5.7 g, 46.3 mmol) was dissolved in diethylether (100 mL) and was treated with a catalytic amount of p-toluensulfonic acid (10 mg). To this was added 3-methyl-2-butenal (2.67 mL, 50.9 mmol) in one portion and the reaction was allowed to stir at ambient temperature for 16 h. The solvent was then evaporated on a rotary evaporator at 0.5 torr to furnish the desired imine (8.7 g, 100%) as a brown oil; $^1$H NMR 300 MHz, CDCl$_3$): δ 8.38 (d, 1H, J=9.5 Hz), 7.11 (dd, 2H, J=2.2, 6.7 Hz), 6.88 (dd, 2H, J=2.2, 6.7 Hz), 6.22–6.18 (m, 1H), 3.81 (s, 3H), 2.01 (s, 3H), 1.95 (s, 3H).

(b) preparation of (±)-cis-N-(4-methoxyphenyl)-3-acetyloxy-4-isobutenylazetidin-2-one

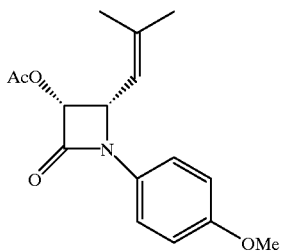

A solution of acetoxyacetyl chloride (6.9 g, 50.5 mmol) was dissolved in ethyl acetate (100 mL) and cooled to −30° C. under an inert atmosphere. To this solution was added triethylamine (7.0 mL, 50.5 mmol) over a 5 min period. The resulting white slurry was then treated with an ethyl acetate solution of N-4-methoxy-N-(3-methyl-2-butenyl) benzenamine (8.7 g, 40 mL) dropwise over a 20 min period. The resulting green-brown slurry was then gradually allowed to warm to ambient temperature over a 4 h period. The slurry was then filtered through a pad of celite and the filtrate was washed with water then brine. The organic fraction was dried (MgSO$_4$) and concentrated to give a brown oil. The crude product was purified by careful silica gel chromatography (eluted with hexanes/ethyl acetate 8:2) to furnish an orange oil which solidified on standing. This was recrystallized from dichloromethane/hexanes to furnish the desired product as a pale yellow solid (4.4 g, 32%); $^1$H NMR (300 MHz, CDCl$_3$): δ 7.32 (d, 2H, J=9.1 Hz), 6.86 (d, 2H, J=9.1 Hz), 5.59 (dd, 1H, J=3.0, 7.8 Hz), 5.14–5.10 (m, 1H), 4.96 (dd, 1H, J=4.8, 9.3 Hz), 3.77 (s, 3H), 2.11 (s, 3H,), 1.81 (s, 3H), 1.78 (s, 3H).

(c) preparation of (±)-cis-3-Acetyloxy-4-isobutenylazetidin-2-one

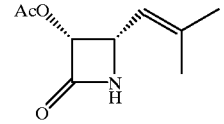

A solution of the (±)-cis-N-(4-methoxyphenyl)-3-acetyloxy-4-isobutenylazetidin-2-one (4.88 g, 16.2 mmol) was dissolved in acetonitrile (50 mL) and cooled to 0–5° C. in an ice bath. To this was added a cold solution of ceric ammonium nitrate (26.6 g, 48.6 mmol, 50 mL) in one portion. The deep red reaction was allowed to stir for 10 min and during that time the color gradually lightened to orange. The cold solution was transferred to a separatory funnel, diluted with water, and extracted with ethyl acetate. The organic fraction was washed with several portions of 10% aqueous sodium sulfite, followed by saturated aqueous sodium bicarbonate. The organic fraction was dried (MgSO$_4$) and concentrated to give the desired product (2.71 g, 91%) as a yellow-orange solid that was used directly in the next step; $^1$H NMR (300 MHz, CDCl$_3$): δ 6.11 (bs, 1H), 5.73 (dd, 1H, J=2.2, 4.7 Hz), 5.12–5.08 (m, 1H), 4.63 (dd, 1H, 4.7, 9.1 Hz), 2.09 (s, 3H), 1.75 (s, 3H), 1.67 (s, 3H).

(d) preparation of (±)-cis-3-Triethylsilyloxy-4-isobutenylazetidin-2-one

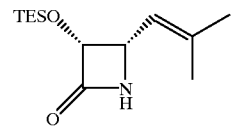

(±)-cis-3-Acetyloxy-4-isobutenylazetidin-2-one (1.47 g, 8.0 mmol) was dissolved in methanol (15 mL) and was V stirred with K$_2$CO$_3$ (110.5 mg, 0.8 mmol) for 3 h at ambient temperature. The solution was then neutralized with Dowex 50W-X8 resin and then filtered. The filtrate was concentrated and the crude solid was dissolved in THF (25 mL) and cooled to 5° C. in an ice bath. Imidazole (544.0 mg, 8.0 mmol) was added and once dissolved, triethylsilyl chloride (1.34 mL, 8.0 mmol) was added dropwise via syringe. The resulting slurry was allowed to warm to ambient temperature and stir overnight. The solution was filtered and the filtrate was washed with water, then brine. The organic fraction was dried (MgSO$_4$) and concentrated. The crude solid was purified by silica gel chromatography (eluted with hexanes/ethyl acetate 3:1) to furnish the desired product (612 mg, 30%) as a pale yellow solid; $^1$H NMR (300 MHz, CDCl$_3$): δ 5.87 (bs, 1H), 5.31–5.26 (m, 1H), 4.90 (dd, 1H, J=2.2, 4.7 Hz), 4.42 (dd, 1H, J=4.7, 9.3 Hz), 1.74 (s, 3H), 1.28 (s, 3H), 0.98–0.91 (m, 9H), 0.71–0.55 (m, 6H).

(e) preparation of (±)-cis-3-Triethylsilyloxy-4-isobutenyl-N-t-butoxycarbonylazetidin-2-one

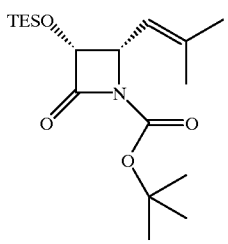

(±)-cis-3-Triethylsilyloxy-4-isobutenylazetidin-2-one (1.01 g, 3.95 mmol) was dissolved in dichloromethane (20 mL) and was treated with diisopropylethylamine (0.68 mL, 3.95 mmol) and a catalytic amount of dimethylaminopyridine. To this solution was added di-t-butyl dicarbonate (1.02 g, 4.68 mmol) and the solution was allowed to stir for 24 h at ambient temperature. The solution was then diluted with additional dichloromethane and washed with water then brine. The organic fraction was dried (MgSO$_4$) and concentrated. The residue was purified by silica gel chromatography (eluted with hexanes/ethyl acetate 8:2) to give the desired product (1.26 g, 90%) as a colorless oil; $^1$H NMR (300 MHz, CDCl$_3$): δ 5.24 (d, 1H, J=9.6 Hz), 4.86 (d, 1H, J=5.7 Hz), 4.72 (dd, 1H, J=6.0, 9.9 Hz), 1.78 (d, 3H, J=1.1 Hz), 1.75 (d, 3H, J=1.1 Hz), 1.47 (s, 9H), 0.96–0.91 (m, 9H), 0.64–0.55 (m, 6H).

Other N-subsituted azetidinones useful in the preparation of compounds of the instant invention may be made by following the teachings of Preparations V to XI.

Preparation XII.
3'-N-debenzoyl-3'-desphenyl-3'-N-(isopropyloxycarbonyl)-3'-(2-furyl)-7-O-methylthiomethylpaclitaxel

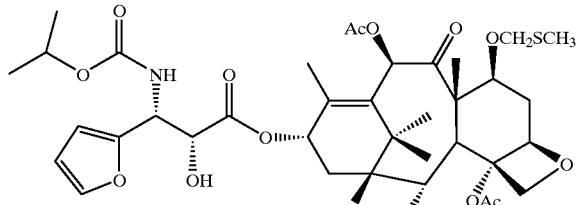

To a solution of the 7-MTM baccatin III (2.0 g, 3.1 mmol) in 40 mL of THF at −60° C. was added LiHMDS (3.7 mL, 1.0M, 3.7 mmol) followed by (3R,4R)-1-(isopropyloxycarbonyl)-4-(2-furyl)-3-(triethylsilyloxy)-2-azetidinone (883 mg, 2.40 mmol) in 25 mL of THF after stirring 10 min. (4.05 g, 11.5 mmol). The solution was brought to 0° C. and stirred for 30 min. The solution was quenched with saturated NH$_4$Cl and extracted with ethyl acetate, dried over MgSO$_4$ and concentrated. The residue was chromatographed over silica gel (2.5:1 hexane/ethyl acetate) to give 2.8 g of silyl ether.

The silyl ether was dissolved in 30 mL of THF as stirred 10 min with Bu$_4$NF (3.0 mL, 1.0M, 3 mmol) diluted with ethyl acetate and washed with brine. The organic fraction was dried (MgSO$_4$), concentrated and the residue purified over silica gel (1:1 hexane/ethyl acetate) to give 2.0 g of the title product (72%).

HRFABMS (NOBA) M+H calcd for $C_{44}H_{56}NO_{16}S$ 886.3320. Found: 886.3345.

IR(film) 3448 (br), 1718, 1372, 1240, 1108, 1066 cm$^{-1}$ $^1$H NMR (CDCl$_3$, 300 MHz) δ 8.08 (d, J=7.2 Hz, 2H), 7.58 (m, 1H), 7.46 (t, J=7.5 Hz, 2H), 7.39 (s, 1H), 6.53 (s, 1H), 6.36 (m, 1H), 6.31 (m, 1H), 6.20 (t, J=8.1 Hz, 1H), 5.66 (d, J=6.9 Hz, 1H), 5.34 (s, 2H), 4.92 (d, J=7.8 Hz, 1H), 4.79 (m, 1H), 4.70 (m, 1H), 4.65 (ABq, J=12, 3.6 Hz, 2H), 4.29 (m, 2H), 4.15 (d, J=8.4 Hz, 1H), 3.86 (d, J=6.9 Hz, 1H), 3.39 (br s, 1H), 2.77 (m, 1H), 2.38 (s, 3H), 2.30 (m, 2H), 2.17 (s, 3H), 2.10 (s, 3H), 2.02 (s, 3H), 1.83 (m, 1H), 1.74 (s, 3H), 1.72 (s, 1H), 1.20–1.10 (m, 12H)

$^{13}$C NMR (CDCl$_3$, 75.5 Hz) δ 201.8, 170.4, 169.2, 167.0, 142.5, 140.2, 133.7, 133.4, 130.2. 129.1, 128.6, 110.7, 107.6, 83.9, 81.3, 78.7, 77.2, 76.1, 75.5, 74.6, 74.0, 72.3, 71.8, 69.1, 57.5, 51.9, 47.2, 43.2, 35.3, 32.9, 26.5 22.5, 22.0, 21.9, 20.9, 15.1, 14.6, 10.9.

EXAMPLE 1
7-O-methylpaclitaxel

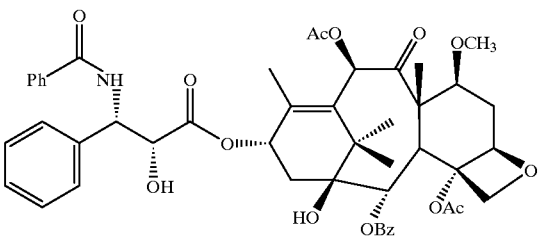

Raney nickel (~0.5 g) was added to a solution of 7-O-methylthiomethylpaclitaxel (73 mg, 0.0799 mmol) in 20 mL of ethyl acetate. This solution was hydrogenated on a Parr apparatus at 50 PSI (pounds per square inch) and ambient temperature for 6 h. Filtration through celite, concentration in vacuo, and purification by flash chromatography over silica gel using 1:2 ethyl acetate:hexane as eluent provided 45 mg (65%) of the title compound as a white foam.

IR (KBr) 3424, 3064, 2928, 1724, 1652, 1602, 1580, 1486, 1316, 1270, 1244, 1178 cm–$^1$ $^1$H NMR (CDCl$_3$) δ 1.203 (s, 6H), 1.203–2.353 (obscured multiplets, 4H), 1749 (s, 3H), 1794 (s, 3H), 2.190 (s, 3H), 2.353 (s, 3H), 2.667 (m, 3H), 3.336 (s, 3H), 3.796 (d, 1H), 4.134 (d, 1H, 4.276 (d, 1H), 4.765 d, 1H), 4.875 (d, 1H), 5.630 (d, 1H), 5.768 (d, 1H), 6.155 (t, 1H), 6.333 (s, 1H), 7.096 (d, 1H), 7.348–8.150 (m, 15H).

MS: [M+Na]$^+$=890; [M+K]$^+$=906

HRMS MH+=$C_{48}H_{53}NO_{14}$ calcd.=868.3544. Found= 868.3511.

EXAMPLE 2
3'-N-Debenzoyl-3'-N-(t-butyloxycarbonyl)-7-O-methylpaclitaxel

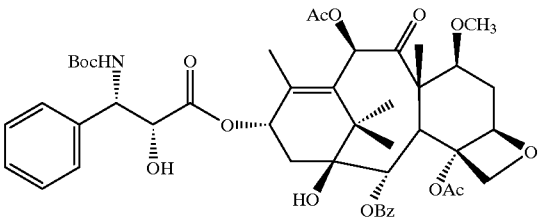

To a solution of 3'-N-debenzoyl-3'-N-(t-butyloxycarbonyl)-7-O-methylthiomethylpaclitaxel (570 mg, 0.63 mmol) in 40 mL of ethanol was added 1–2 g of wet Raney Nickel. The suspension was refluxed for 20 min and filtered through Celite and washed with ethyl acetate. The filtrate was concentrated and the residue chromatographed over silica gel (1:1 hexane/ethyl acetate) to give 424 mg of the title compound (78%).

HRFABMS (NOBA) M+H calcd for $C_{46}H_{58}NO_{15}$: 864.3807 Found: 864.3797.

IR (film) 3442, 1726, 1370, 1244, 1170, 1106, 1070 cm$^{-1}$.

$^1$H NMR (CDCl$_3$, 300 MHz) δ 8.07 (t, J=7.2 Hz, 2H), 7.58 (m, 1H), 7.46 (t, J=7.8 Hz, 2H), 7.34 (m, 5H), 6.40 (s, 1H), 6.16 (d, J=9.0 Hz, 1H), 5.63 (d, J=6.9 Hz, 1H), 5.40 (d, J=9.4 Hz, 1H), 5.25 (m, 1H), 4.94 (d, J=7.8 Hz, 1H), 4.59 (m, 1H), 4.27 (d, J=8.3 Hz, 1H), 4.14 (d, J=8.3 Hz, 1H), 3.84 (m, 2H), 3.41 (d, J=5.3 Hz, 1H), 3.32 (s, 3H), 2.70 (m, 1H), 2.41 (s, 3H), 2.27 (d, J=8.3 Hz, 2H), 2.20 (s, 3H), 1.87 (s, 3H), 1.76 (m, 1H), 1.70 (s, 3H), 1.33 (s, 9H), 1.20 (s, 3H), 1.19 (s, 3H).

$^{13}$C NMR (CDCl$_3$, 75.5 Hz) δ 202.2, 170.4, 169.4, 167.0, 155.3, 140.0, 133.7, 130.1, 129.1, 128.8, 128.7, 128.1, 126.7. 84.1, 81.6, 80.4, 80.2, 78.6, 74.7, 74.5, 73.6, 72.4, 57.6, 57.2, 47.2, 43.3, 35.3, 32.3, 28.2, 26.6, 22.7, 21.1, 21.0, 14.6, 10.4.

EXAMPLE 3
3'-N-Debenzoyl-3'-N-(t-butyloxycarbonyl)-7-O-methoxymethylpaclitaxel

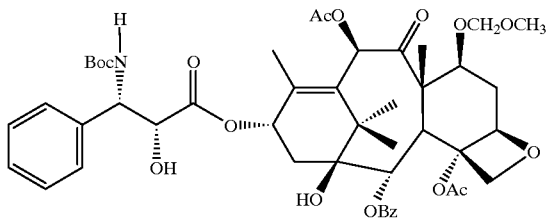

To a solution of the 3'-N-debenzoyl-3'-N-(t-butyloxycarbonyl)-7-O-methylthiomethyl-2'-O-triethylsilylpaclitaxel (48 mg, 0.047 mmol) in 1 mL of dichloromethane was added methanol (20 mg, 0.6 mmol) and the solution cooled to 0° C. Then NIS (13 mg, 0.058 mmol) and triethylsilyltriflate (1 μL, 0.004 mmol) were added and the dark red solution stirred 30 minutes and then warmed to 25° C. for 30 minutes. The solution was diluted with ethyl acetate and washed with 10% Na$_2$S$_2$O$_3$ and bicarbonate, dried (MgSO$_4$) and concentrated. (Note: Under this reaction condition, triethylsilyl group is cleaved from 2'-O-position.) The residue was chromatographed over silica gel (1:1 hexane/ethyl acetate) to give 32 mg of the title compound (76%).

FABMS (NOBA) M+H calcd for $C_{47}H_{60}NO_{17}$: 894. Found: 894.

IR (film) 3440, 1722, 1370, 1242, 1106, 1068, 1026 cm$^{-1}$.

$^1$H NMR (CDCl$_3$, 300 MHz) δ 8.07 (d, J=7.3 Hz, 2H), 7.59 (t, J=7.3 Hz, 1H), 7.46 (t, J=7.8 Hz, 2H), 7.36 (m, 5H), 6.33 (s, 1H), 6.16 (t, J=8.8 Hz, 1H), 5.64 (d, J=6.9 Hz, 1H), 5.40 (d, J=9.5 Hz, 1H), 5.24 (br d, J=8.1 Hz, 1H), 4.90 (d, J=7.9 Hz, 1H), 4.68 (d, J=7.6 Hz, 1H), 4.62 (d, J=7.6 Hz, 1H), 4.28 (d, J=8.4 Hz, 1H), 4.14 (d, J=8.2 Hz, 1H), 4.08 (m, 1H), 3.82 (d, J=6.8 Hz, 1H), 3.40 (d, J=5.2 Hz, 1H), 3.27 (s, 3H), 2.77(m, 1H), 2.33 (s, 3H), 2.27 (d, J=8.9 Hz, 2H), 2.19 (s, 3H), 1.94 (m, 1H), 1.86 (s, 3H), 1.73 (s, 3H), 1.72 (m, 1H), 1.63 (br s, 1H), 1.32 (s, 9H), 1.20 (c, 3H), 1.19 (s, 3H)

$^{13}$C NMR (CDCl$_3$, 75.5 Hz) δ 202.2, 172.7, 170.2, 169.4, 167.0, 155.3, 140.2, 138.3, 133.7, 133.3, 130.2, 129.1, 128.8, 128.7, 128.1, 126.8, 98.2, 84.3, 81.2, 80.2, 79.9, 78.6, 75.3, 74.5, 73.6, 72.3, 57.3, 56.1, 55.8, 46.9, 43.2, 35.4, 35.3, 28.2, 26.5, 22.6, 20.9, 14.7, 10.7.

EXAMPLE 4
3'-N-Debenzoyl-3'-N-(t-butyloxycarbonyl)-7-O-[(2-hydroxyethoxy)methyl]paclitaxel

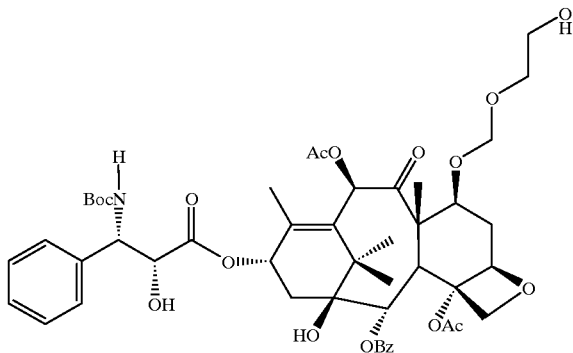

To a solution of 3'-N-debenzoyl-3'-N-(t-butyloxycarbonyl)-7-O-methylthiomethylpaclitaxel (47 mg, 0.052 mmol) and ethylene glycol (20 mg. 0.32 mmol) in 1 mL of dichloromethane was added NIS (14 mg, 0.062 mmol) and triethylsilyltriflate (1 μL, 0.004 mmol). The solution was stirred for 15 minutes. The solution was diluted with ethyl acetate and washed with 10% Na$_2$S$_2$O$_3$, dried (MgSO$_4$) and concentrated. The residue was chromatographed over silica gel (1:1 hexane/ethyl acetate with 5% methanol) to give 37 mg of the title compound (77%).

FABMS (NOBA) M+Na calcd for $C_{48}H_{61}NO_{17}$Na 946. Found: 946.

IR (film) 3440, 1720, 1242, 1070, 1026, 756 cm$^{-1}$.

$^1$H NMR (CDCl$_3$, 300 MHz) δ 8.06 (d, J=7.5 Hz, 2H), 7.58 (t, J=7.2 Hz, 1H), 7.46 (t, J=7.8 Hz, 2H), 7.31 (m, 5H), 6.35 (s, 1H), 6.15 (t, J=8.7 Hz, 1H) 5.63 (d, J=6.9 Hz, 1H), 5.44 (br d, J=9.2, 1H), 5.24 (br s, 1H), 4.90 (d, J=8.4 Hz, 1H), 4.74 (s, 2H), 4.59 (br s, 1H), 4.27 (d, J=8.4 Hz, 1H), 4.11 (m, 2H), 3.81 (d, J=6.8 Hz, 1H), 3.66 (m, 3H), 3.48 (m, 2H), 2.75 (m, 1H), 2.33 (s, 3H), 2.26 (m, 2H), 2.18 (s, 3H), 1.90 (m, 2H), 1.87 (s, 3H), 1.78 (m, 1H), 1.72 (s, 3H), 1.32 (s, 9H), 1.19 (s, 3H), 1.18 (s, 3H).

$^{13}$C NMR (CDCl$_3$, 75.5 Hz) δ 202.1, 172.8, 170.3, 169.6, 167.0, 155.3, 140.2, 138.3, 133.7, 133.3, 130.2, 129.1, 128.8, 128.7, 128.0. 126.8, 96.8. 84.1, 81.2, 80.2, 79.4, 78.6, 76.5, 75.2, 74.5, 73.6, 72.3, 70.0, 61.8, 57.3, 56.2, 46.9, 43.2, 35.3, 35.0, 28.2, 26.5, 22.6, 21.0, 20.9, 14.6, 10.6.

EXAMPLE 5
3'-N-Debenzoyl-3'-desphenyl-3'-N-(t-butyloxycarbonyl)-3'-(2-furyl)-7-O-methylpaclitaxel

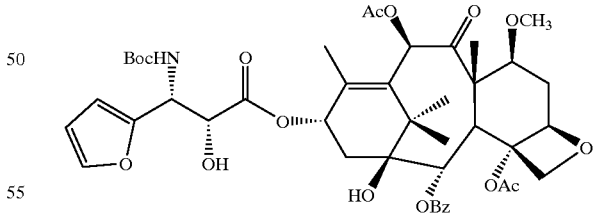

To a solution of 3'-N-debenzoyl-3'-desphenyl-3'-N-(t-butyloxycarbonyl)-3'-(2-furyl)-7-O-methylthiomethylpaclitaxel (360 mg, 0.4 mmol) in 40 mL of ethanol was added 0.5–1.5 g of wet Raney Nickel. The suspension was refluxed for 90 min. and filtered through Celite and washed with ethyl acetate. The filtrate was concentrated and the residue chromatographed over silica gel (1:1 hexane/ethyl acetate) to give 106 mg of recovered 7-MTM ether and 68 mg (28%) of 7-O-methylbaccatin III and 57 mg (16%) of the title compound.

HRFABMS (NOBA) M+H calcd for $C_{44}H_{56}NO_{16}$: 854.3599 Found: 854.3608.

IR (film) 3440, 1722, 1268, 1244, 1106, 756 cm$^{-1}$.

$^1$H NMR (CDCl$_3$, 300 MHz) δ 8.07 (t, J=7.2 Hz, 2H), 7.58 (t, J=7.3, 1H), 7.46 (t, J=7.7 Hz, 2H), 7.39 (m, 1H), 6.42 (s, 1H), 6.35 (m, 1H), 6.30 (m, 1H), 6.18 (t, J=7.6 Hz, 1H), 5.64 (d, J=7.0 Hz, 1H), 5.28 (m, 2H), 4.95 (d, J=7.8 Hz, 1H), 4.69 (dd, J=5.8, 2.1 Hz, 1H), 4.28 (d, J=8.3 Hz, 1H), 4.13 (d, J=8.3 Hz, 1H), 3.86 (m, 2H), 3.36 (d, J=5.6 Hz, 1H), 3.32 (s, 3H), 2.70 (m, 1H), 2.38 (s, 3H), 2.32 (d, J=8.9 Hz, 2H), 2.20 (s, 3H), 1.94 (s, 3H), 1.76 (m, 2H), 1.69 (m, 3H), 1.34 (s, 9H), 1.20 (s, 3H), 1.19 (s, 3H).

$^{13}$C NMR (CDCl$_3$, 75.5 Hz) δ 202.2, 172.6, 170.4, 169.4, 167.1, 155.2, 151.3, 142.4, 140.0, 133.7, 130.2, 129.1, 128.7, 110.7, 107.5, 84.1, 81.5, 80.4, 78.6, 76.5, 74.7, 74.5, 72.5, 71.8, 57.6, 57.2, 51.7, 47.2, 43.3, 35.2, 32.3, 28.1, 26.5, 22.6, 21.1, 20.9, 14.6, 10.3.

EXAMPLE 6
3'-N-Debenzoyl-3'-desphenyl-3'-N-(t-butyloxycarbonyl)-3'-(2-furyl)-7-O-methoxymethylpaclitaxel

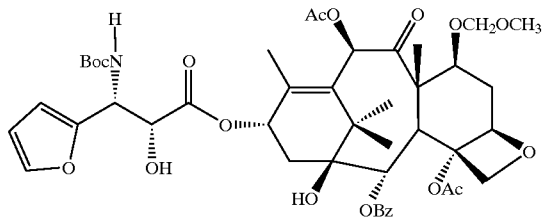

To a solution of 3'-N-debenzoyl-3'-desphenyl-3'-N-(t-butyloxycarbonyl)-3'-(2-furyl)-7-O-methylthiomethyl-2'-O-triethylsilylpaclitaxel (65 mg, 0.064 mmol) and methanol (20 mg. 0.6 mmol) in 1 mL of dichloromethane at 0° C. was added NIS (16 mg, 0.071 mmol) and triethylsilyltriflate (1 μL, 0.004 mmol). The solution was stirred at 0° C. for 30 minutes and then brought to 25° C. for 45 minutes. The solution was diluted with ethyl acetate and washed with saturated NaHSO$_3$, dried (MgSO$_4$) and concentrated. The residue was chromatographed over silica gel (1:1 hexane/ethyl acetate) to give 26 mg of the title compound (46%).

FABMS (NOBA) M+H calcd for $C_{45}H_{58}NO_{17}$: 884. Found: 884.

IR (film) 3442, 1720, 1268, 1242, 1040, 1026, 756 cm$^{-1}$.

$^1$H NMR (CDCl$_3$, 300 MHz) δ 8.08 (d, J=7.2 Hz, 2H), 7.58 (t, J=7.3 Hz, 1H), 7.46 (t, J=7.8 Hz, 2H), 7.39 (s, 1H), 6.35 (m, 2H), 6.30 (d, J=3.2 Hz, 1H), 6.17 (t, J=8.2 Hz, 1H) 5.65 (d, J=6.9 Hz, 1H), 5.32 (d, J=9.6 Hz, 1H), 5.24 (d, J=9.8 Hz, 1H), 4.91 (d, J=8.0 Hz, 1H), 4.69 (m, 2H), 4.62 (d, J=7.5 Hz, 1H), 4.29 (d, J=8.4 Hz, 1H), 4.10 (m, 2H), 3.84 (d, J=6.9 Hz, 1H), 3.33 (d, J=5.7 Hz, 1H), 3.27 (s, 3H), 2.77 (m, 1H), 2.37 (s, 3H), 2.31 (d, J=9.0 Hz, 2H), 2.18 (s, 3H), 1.93 (m, 4H), 1.73 (m, 5H), 1.34 (s, 9H), 1.19 (s, 6H).

$^{13}$C NMR (CDCl$_3$, 75.5 Hz) δ 202.2, 172.6, 170.2, 169.4, 167.0, 155.2, 151.3, 142.5, 140.2, 133.7, 133.3, 130.2, 129.1, 128.7, 110.7, 107.5, 98.2, 84.3, 81.1, 80.5, 79.8, 78.6, 75.3, 74.6, 72.5, 71.7, 57.4, 55.8, 51.7, 46.9, 43.2, 35.4, 35.2, 28.1, 26.4, 22.6, 21.0, 20.9, 14.6, 10.7.

EXAMPLE 7
3'-N-Debenzoyl-3'-desphenyl-3'-N-(t-butyloxycarbonyl)-3'-(2-furyl)-7-O-[(2-hydroxyethoxy)methyl]paclitaxel

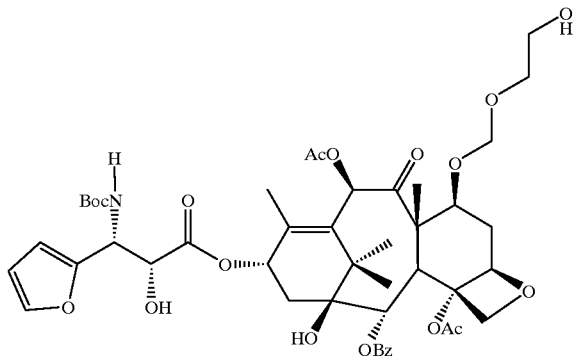

To a solution of the 3'-N-debenzoyl-3'-desphenyl-3'-N-(t-butyloxycarbonyl)-3'-(2-furyl)-7-O-methylthiomethylpaclitaxel (59 mg, 0.065 mmol) and ethylene glycol (20 mg. 0.32 mmol) in 1 mL of dichloromethane was added NIS (17 mg, 0.076 mmol) and triethylsilyltriflate (1 μL, 0.004 mmol). The solution was stirred for 15 minutes. The solution was diluted with ethyl acetate and washed with 10% Na$_2$S$_2$O$_3$, dried (MgSO$_4$) and concentrated. The residue was chromatographed over silica gel (1:1 hexane/ethyl acetate 2% methanol) to give 39.4 mg of the title compound (66%).

FABMS (NOBA) M+Na calcd for $C_{45}H_{59}NO_{18}$: 936. Found: 936.

IR (film) 3440, 1722, 1370, 1244, 1166, 1108, 1070, 1050, 1026 cm$^{-1}$.

$^1$H NMR (CDCl$_3$, 300 MHz) δ 8.07 (d, J=7.3 Hz, 2H), 7.58 (t, J=7.3 Hz, 1H), 7.46 (t, J=7.8 Hz, 2H), 7.39 (d, J=1.7 Hz, 1H), 6.37 (s, 1H), 6.35 (m, 1H), 6.30 (d, J=3.2 Hz, 1H), 6.16 (t, J=8.3 Hz, 1H), 5.64 (d, J=6.9 Hz, 1H), 5.27 (m, 2H), 4.91 (d, J=8.0 Hz, 1H), 4.73 (m, 3H), 4.28 (d, J=8.3 Hz, 1H), 4.16 (m, 2H), 3.84 (d, J=6.9 Hz, 1H), 3.65 (m, 3H), 3.46 (m, 2H), 2.77 (m, 1H), 2.37 (s, 3H), 2.32 (m, 3H), 2.18 (s, 3H), 1.93 (m, 4H), 1.72 (m, 4H), 1.33 (s, 9H), 1.19 (s, 6H).

$^{13}$C NMR (CDCl$_3$, 75.5 Hz) δ 202.1, 172.6, 170.4, 169.6, 167.0, 155.2, 151.3, 142.4, 140.2, 133.7, 133.4, 130.2, 129.1, 128.7, 110.7, 107.5, 96.7, 84.2, 81.1, 80.5, 79.4, 78.6, 76.5, 75.3, 74.5, 72.4, 71.7, 70.0, 61.8, 57.3, 51.7, 47.0, 43.3, 35.2, 35.0, 28.1, 26.4, 22.6, 21.1, 20.9, 14.6, 10.7.

EXAMPLES 8–22

Following the teachings contained herein, the following compounds in Examples 8–22 were prepared.

(I)

[Structure of compound I with substituents AcO, OCH₂R¹, R⁴(O)ₚCONH, R⁵, R², HO, AcO, OCOPh]

| Example No. | R⁴(O)ₚ | R⁵ | R² | R¹ |
|---|---|---|---|---|
| 8 | tBuO | Ph | OCO₂Et | OCH₃ |
| 9 | tBuO | Ph | OCO₂Et | OCH₂CH₂OH |
| 10 | tBuO | 2-furyl | OCO₂Et | H |
| 11 | tBuO | Ph | OCO₂Et | H |
| 12 | tBuO | 2-furyl | OH | O(CH₂)₄OH |
| 13 | tBuO | 2-furyl | OH | O(CH₂)₅OH |
| 14 | tBuO | 2-furyl | OH | O(CH₂)₃OH |
| 15 | tBuO | 2-furyl | OCO₂Et | OCH₂CH₂OH |
| 16 | (CH₃)₂CHO | 2-furyl | OCO₂Et | OCH₂CH₂OH |
| 17 | (CH₃)₂CHO | 2-furyl | OH | OCH₂CH₂OH |
| 18 | (CH₃)₂CHO | 2-furyl | OH | O(CH₂)₅OH |
| 19 | (CH₃)₂CHO | 2-furyl | OH | O(CH₂)₆OH |
| 20 | (CH₃)₂CHO | 2-furyl | OH | O(CH₂)₇OH |
| 21 | tBuO | (CH₃)₂CHCH₂ | OH | H |
| 22 | Ph | 2-furyl | OH | H |

EXAMPLE 8

2'-O-Ethoxycarbonyl-3'-N-debenzoyl-3'-N-(t-butyloxycarbonyl)-7-O-methoxymethylpaclitaxel HRFABMS (NOBA) M+H calcd for $C_{50}H_{64}NO_{18}$ 966.4123. Found: 966.4102.

IR (film) 1750, 1722, 1370, 1244, 1040 cm⁻¹

¹H NMR (CDCl₃, 300 MHz) δ 8.09 (d, J=7.2 Hz, 2H), 7.59 (t, J=7.5 Hz, 1H), 7.48 (t, J=7.3 Hz, 2H), 7.35 (m, 5H), 6.37 (s, 1H), 6.23 (t, J=8.7 Hz, 1H), 5.68 (d, J=6.9 Hz, 1H), 5.40 (br s, 2H), 5.23 (s, 1H), 4.93 (d, J=8.1 Hz, 1H), 4.69 (d, J=7.5 Hz, 1H), 4.63 (d, J=7.5 Hz, 1H), 4.30 (d, J=8.4 Hz, 1H), 4.17 (m, 4H), 3.87 (d, J=6.6 Hz, 1H), 3.28 (s, 3H), 2.79 (m, 1H), 2.42 (s, 3H), 2.32 (m, 1H), 2.18 (s, 3H), 1.99 (s, 3H), 1.96 (m, 1H), 1.74 (s, 3H), 1.68 (s, 1H), 1.61 (s, 1H), 1.33 (s, 9H), 1.27 (t, J=7.2 Hz, 3H), 1.21 (s, 3H), 1.19 (s, 3H).

¹³C NMR (CDCl₃, 75.5 Hz) δ 202.3, 169.5, 169.3, 168.2, 167.0, 155.1, 154.1, 140.9, 137.2, 133.6, 132.9 130.2, 129.2, 128.9, 128.7, 128.2, 126.4, 98.3, 84.4, 81.1, 80.4, 79.8, 78.8, 76.4, 75.2, 74.8, 72.0, 65.1, 57.3, 55.8, 54.2, 46.9, 43.3, 35.4, 35.1, 28.1, 26.4, 22.7, 21.4, 20.9, 14.5, 14.1, 10.7

EXAMPLE 9

2'-O-Ethoxycarbonyl-3'-N-debenzoyl-3'-N-(t-butyloxycarbonyl)-7-O-[(2-hydroxyethoxy)methyl]paclitaxel HRFABMS (NOBA) M+H calcd for $C_{51}H_{66}NO_{19}$ 996.4229. Found: 996.4198.

IR (film) 3502, 1750, 1722, 1372, 1244, 1026 cm⁻¹

¹H NMR (CDCl₃, 300 MHz) δ 8.09 (d, J=7.2 Hz, 2H), 7.59 (t, J=7.5 Hz, 1H), 7.48 (t, J=7.3 Hz, 2H), 7.35 (m, 5H), 6.39 (s, 1H), 6.23 (t, J=8.7 Hz, 1H), 5.67 (d, J=6.9 Hz, 1H), 5.40 (br s, 2H), 5.23 (s, 1H), 4.93 (d, J=8.1 Hz, 1H), 4.77 (d, J=7.5 Hz, 1H), 4.74 (d, J=7.5 Hz, 1H), 4.30 (d, J=8.4 Hz, 1H), 4.17 (m, 4H), 3.86 (d, J=6.6 Hz, 1H), 2.79 (m, 1H), 2.42 (s, 3H), 2.32 (m, 1H), 2.18 (s, 3H), 1.99 (s, 3H), 1.93 (m, 1H), 1.73 (s, 3H), 1.69 (s, 1H), 1.62 (s, 1H), 1.33 (s, 9H), 1.27 (t, J=7.2 Hz, 3H), 1.21 (s, 3H), 1.19 (s, 3H).

¹³C NMR (CDCl₃, 75.5 Hz) δ 202.1, 169.7, 169.5, 168.2, 167.0, 155.1, 154.1, 140.9, 137.2, 135.0, 133.7, 133.0, 130.2, 129.2, 128.9, 128.7, 128.2, 126.4, 96.9, 84.2, 81.1, 80.4, 79.5, 78.8, 76.4, 75.2, 74.7, 72.0, 70.0, 65.1, 61.8, 57.2, 54.2, 46.9, 43.3, 35.1, 28.1, 26.4, 22.7, 21.4, 20.9, 14.5, 14.1, 10.7, 9.8.

EXAMPLE 10

2'-O-Ethoxycarbonyl-3'-N-debenzoyl-3'-desphenyl-3'-N-(t-butyloxycarbonyl)-3'-(2-furyl)-7-O-methylpaclitaxel HRFABMS (NOBA) M+H calcd for $C_{47}H_{60}NO_{18}$ 926.3810. Found: 926.3823.

IR (film) 3380, 1752, 1722, 1242 cm⁻¹

¹H NMR (CDCl₃, 300 MHz) δ 8.08 (d, J=7.2 Hz, 2H), 7.58 (t, J=7.5 Hz, 1H), 7.46 (t, J=7.8 Hz, 2H), 7.39 (s, 1H), 6.44 (s, 1H), 6.35 (m, 1H), 6.28 (m, 1H), 6.20 (t, J=9.0 Hz, 1H), 5.65 (d, J=6.9 Hz, 1H), 5.51 (br d, J=9.9 Hz, 1H), 5.33 (s, 1H), 5.25 (br d, J=10.2 Hz, 1H), 4.97 (d, J=8.1 Hz, 1H), 4.29 (d, J=8.1 Hz, 1H), 4.17 (m, 3H), 3.88 (m, 2H), 3.33 (s, 3H), 2.72 (m, 1H), 2.41 (s, 3H), 2.31 (m, 1H), 2.18 (s, 3H), 2.01 (s, 3H), 1.76 (m, 1H), 1.70 (s, 3H), 1.67 (s, 1H), 1.60 (s, 1H), 1.34 (s, 9H), 1.29 (s, 1H), 1.27 (t, J=7.2 Hz, 1H), 1.19 (s, 6H).

¹³C NMR (CDCl₃, 75.5 Hz) δ 202.4, 169.9, 169.3, 167.7, 167.0, 155.0, 154.0, 150.0, 142.6, 140.8, 133.6, 133.2, 130.2, 129.2, 128.7, 110.7, 107.6, 84.1, 81.4, 80.7, 80.4, 78.7, 76.4, 75.1, 74.8, 74.6, 71.9, 65.1, 57.6, 57.1, 49.7, 47.2, 43.3, 35.0, 32.3, 28.1, 26.4, 22.6, 21.3, 20.9, 14.6, 14.1, 10.4.

EXAMPLE 11

2'-O-Ethoxycarbonyl-3'-N-debenzoyl-3'-N-(t-butyloxycarbonyl)-7-O-methylpaclitaxel HRFABMS (NOBA) M+H calcd for $C_{49}H_{62}NO_{17}$ 936.4018. Found: 936.4058.

IR (film) 3448, 1750, 1724, 1370, 1244, 1172 cm⁻¹

¹H NMR (CDCl₃, 300 MHz) δ 8.09 (d, J=7.2 Hz, 2H), 7.59 (t, J=7.5 Hz, 1H), 7.48 (t, J=7.3 Hz, 2H), 7.35 (m, 5H), 6.43 (s, 1H), 6.23 (t, J=8.7 Hz, 1H), 5.65 (d, J=6.9 Hz, 1H), 5.40 (br s, 2H), 5.20 (s, 1H), 4.96 (d, J=8.1 Hz, 1H), 4.30 (d, J=8.4 Hz, 2H), 4.16 (m, 3H), 3.88 (m, 2H), 3.33 (s, 3H), 2.70 (m, 1H), 2.42 (s, 3H), 2.31 (m, 1H), 2.19 (s, 3H), 1.76 (m, 1H), 1.70 (s, 3H), 1.67 (s, 1H), 1.60 (s, 1H), 1.33 (s, 9H), 1.27 (t, J=7.2 Hz, 3H), 1.21 (s, 3H), 1.19 (s, 3H).

¹³C NMR (CDCl₃, 75.5 Hz) δ 202.3, 169.7, 169.3, 168.2, 167.0, 155.1, 154.1, 140.8, 137.2, 133.7, 133.2, 130.2, 129.2, 128.9, 128.7, 128.2, 126.4, 84.2, 81.4, 80.4, 78.9, 76.4, 74.7, 74.7, 72.1, 65.1, 57.6, 57.0, 54.1, 47.2, 43.3, 35.0, 32.2, 28.1, 26.5, 22.7, 21.5, 20.9, 14.5, 14.1, 10.4.

EXAMPLE 12

3'-N-Debenzoyl-3'-desphenyl-3'-N-(t-butyloxycarbonyl)-3'-(2-furyl)-7-O-[(4-hydroxybutyloxy)methyl]paclitaxel HRFABMS (NOBA) M+H calcd for $C_{48}H_{64}NO_{18}$ 942.4123. Found: 942.4112.

IR (film) 3450, 1718, 1242 cm⁻¹

¹H NMR (CDCl₃, 300 MHz) δ 8.08 (d, J=7.2 Hz, 2H), 7.58 (t, J=7.5 Hz, 1H), 7.46 (t, J=7.8 Hz, 2H), 7.39 (s, 1H), 6.35 (m, 2H), 6.30 (s, 1H), 6.17 (t, J=9.6 Hz, 1H), 5.65 (d, J=6.9 Hz, 1H), 5.27 (br m, 2H), 4.92 (d, J=7.8 Hz, 1H), 4.71 (m, 2H), 4.29 (d, J=8.4 Hz, 1H), 4.14 (m, 2H), 3.84 (d, J=6.8 Hz, 1H), 3.61 (m, 3H), 3.39 (s, 1H), 2.79 (m, 1H), 2.37 (s, 3H), 2.32 (d, J=9.0 Hz, 2H), 2.19 (s, 3H), 1.96 (m, 1H), 1.93 (s, 3H), 1.72 (s, 3H), 1.62 (m, 8H), 1.34 (s, 9H), 1.20 (s, 3H), 1.19 (s, 3H).

³C NMR (CDCl₃, 75.5 Hz) δ 202.1, 172.6, 170.3, 169.4, 167.0, 151.3, 142.4, 140.2, 133.7, 133.4, 130.2, 129.1, 128.7, 110.7, 108.3, 107.4, 96.8, 84.3, 81.2, 80.5, 79.7, 78.6, 77.2, 75.2, 74.6, 72.4, 72.4, 71.8, 68.2, 62.6, 57.4, 53.0, 51.4, 46.9, 43.3, 42.0, 35.2, 33.1, 29.7, 28.1, 26.4, 26.1, 22.6, 21.0, 20.9, 14.7, 12.6, 10.6.

EXAMPLE 13
3'-N-Debenzoyl-3'-desphenyl-3'-N-(t-butyloxycarbonyl)-3'-(2-furyl)-7-O-[(5-hydroxypentyloxy)methyl]paclitaxel HRFABMS (NOBA) M+H calcd for $C_{49}H_{66}NO_{18}$ 956.4290. Found: 956.4290.

IR (film) 3441, 1721, 1169 cm$^{-1}$ $^1$H NMR (CDCl$_3$, 300 MHz) δ 8.07 (d, J=7.2 Hz, 2H), 7.58 (t, J=7.5 Hz, 1H), 7.46 (t, J=7.8 Hz, 2H), 7.38 (s, 1H), 6.34 (m, 2H), 6.30 (s, 1H), 6.17 (t, J=9.6 Hz, 1H), 5.64 (d, J=6.9 Hz, 1H), 5.32 (s, 2H), 4.92 (d, J=7.8 Hz, 1H), 4.69 (s, 3H), 4.29 (d, J=8.4 Hz, 1H), 4.16 (m, 2H), 3.84 (d, J=6.8 Hz, 1H), 3.56 (m, 4H), 3.38 (m, 1H), 2.79 (m, 1H), 2.37 (s, 3H), 2.30 (d, J=8.7 Hz, 2H), 2.18 (s, 3H), 1.93 (s, 4H), 1.75 (m, 3H), 1.72 (s, 3H), 1.54 (m, 5H), 1.42 (m, 2H), 1.35 (s, 9H), 1.19 (s, 6H).

$^{13}$C NMR (CDCl$_3$, 75.5 Hz) δ 202.1, 172.4, 170.7, 169.4, 166.9, 151.4, 142.4, 140.2, 133.7, 133.4, 130.1, 130.1, 129.2, 128.6, 110.6, 107.4, 96.2, 84.3, 81.3, 80.4, 78.9, 78.6, 75.3, 74.6, 72.2, 71.9, 68.2, 62.8, 57.3, 51.8, 46.9, 43.2, 35.3, 34.9, 32.5, 29.3, 28.2, 26.5, 22.6, 21.0, 20.9, 14.8, 10.6.

EXAMPLE 14
3'-N-Debenzoyl-3'-desphenyl-3'-N-(t-butyloxycarbonyl)-3'-(2-furyl)-7-O-[(3-hydroxypropyloxy)methyl]paclitaxel HRFABMS (NOBA) M+H calcd for $C_{47}H_{62}NO_{18}$ 928.3967. Found: 928.3987.

IR (film) 3441, 1718, 1242, 1108, 1049 cm$^{-1}$ $^1$H NMR (CDCl$_3$, 300 MHz) δ 8.07 (d, J=7.2 Hz, 2H), 7.57 (t, J=7.5 Hz, 1H), 7.45 (t, J=7.8 Hz, 2H), 7.39 (s, 1H), 6.35 (m, 2H), 6.30 (s, 1H), 6.16 (t, J=9.6 Hz, 1H), 5.64 (d, J=6.9 Hz, 1H), 5.30 (s, 2H), 4.90 (d, J=7.8 Hz, 1H), 4.70 (s, 3H), 4.28 (d, J=8.4 Hz, 1H), 4.12 (m, 2H), 3.84 (d, J=6.8 Hz, 1H), 3.73 (m, 3H), 3.49 (m, 2H), 2.76 (m, 1H), 2.37 (s, 3H), 2.32 (d, J=9.0 Hz, 2H), 2.18 (s, 3H), 1.97 (s, 2H), 1.92 (s, 3H), 1.76 (m, 6H), 1.33 (s, 9H), 1.19 (s, 6H).

$^{13}$C NMR (CDCl$_3$, 75.5 Hz) δ 202.1, 172.6, 170.3, 169.5, 167.0, 155.2, 151.3, 142.4, 140.2, 133.7, 133.4, 130.2, 129.1, 128.7, 110.7, 107.5, 96.8, 84.3, 81.1, 80.5, 79.6, 78.6, 77.2, 76.4, 75.2, 74.6, 72.4, 71.8, 66.7, 61.0, 57.3, 51.7, 46.9, 43.3, 35.2, 32.1, 29.5, 28.1, 26.4, 22.6, 21.1, 20.9, 14.7, 10.6.

EXAMPLE 15
2'-O-Ethoxycarbonyl-3'-N-debenzoyl-3'-desphenyl-3'-N-(t-butyloxycarbonyl)-3'-(2-furyl)-7-O-[(2-hydroxyethoxy)methyl]paclitaxel HRFABMS (NOBA) M+H calcd for $C_{49}H_{64}NO_{20}$ 986.4022. Found: 986.4067.

IR (film) 3449, 1753, 1722, 1372, 1242, 1039, 1026 cm$^{-1}$ $^1$H NMR (CDCl$_3$, 300 MHz) δ 8.08 (d, J=7.2 Hz, 2H), 7.58 (t, J=7.5 Hz, 1H), 7.46 (t, J=7.8 Hz, 2H), 7.39 (s, 1H), 6.39 (s, 1H), 6.35 (m, 1H), 6.28 (m, 1H), 6.21 (t, J=9.6 Hz, 1H), 5.65 (d, J=6.9 Hz, 1H), 5.51 (br d, J=10.5 Hz, 1H), 5.32 (s, 1H), 5.26 (br d, J=9.9 Hz, 1H), 4.93 (d, J=7.8 Hz, 1H), 4.73 (ABq, J=7.5, 3.9 Hz, 2H), 4.30 (d, J=8.4 Hz, 1H), 4.17 (m, 4H), 3.87 (d, J=6.8 Hz, 1H), 3.69 (m, 3H), 3.51 (m, 1H), 2.78 (m, 1H), 2.41 (s, 3H), 2.30 (m, 2H), .2.17 (s, 4H), 2.00 (s, 3H), 1.93 (m, 1H), 1.73 (s, 3H), 1.69 (s, 1H), 1.34 (s, 9H), 1.29 (t, J=7.2 Hz, 3H), 1.19 (s, 6H).

$^{13}$C NMR (CDCl$_3$, 75.5 Hz) δ 202.2, 169.9, 169.5, 167.7, 167.0, 155.1, 154.0, 150.1, 142.6, 140.9, 133.7, 132.9, 130.2, 128.7, 110.7, 107.6, 97.0, 84.2, 81.0, 80.7, 79.6, 78.7, 77.2, 76.4, 75.3, 75.1, 74.7, 71.9, 70.0, 65.1, 61.8, 57.2, 49.7, 47.0, 43.3, 35.1, 35.0, 28.1, 26.3, 22.6, 21.2, 20.9, 14.8, 14.6, 14.1, 10.6.

EXAMPLE 16
2'-O-Ethoxycarbonyl-3'-N-debenzoyl-3'-desphenyl-3'-N-(isopropyloxycarbonyl)-3'-(2-furyl)-7-O-[(2-hydroxyethoxy)methyl]paclitaxel HRFABMS (NOBA) M+H calcd for $C_{48}H_{62}NO_{20}$ 972.3865. Found: 972.3895.

IR (film) 3510, 1752, 1722, 1244 cm$^{-1}$ $^1$H NMR (CDCl$_3$, 300 MHz) δ 8.08 (d, J=7.2 Hz, 2H), 7.58 (t, J=7.5 Hz, 1H), 7.46 (t, J=7.8 Hz, 2H), 7.39 (s, 1H), 6.38 (s, 1H), 6.35 (m, 1H), 6.28 (m, 1H), 6.22 (t, J=9.6 Hz, 1H), 5.66 (d, J=6.9 Hz, 1H), 5.52 (br d, J=10.5 Hz, 1H), 5.33 (s, 1H), 5.31 (br d, J=10.0 Hz, 1H), 4.93 (d, J=7.8 Hz, 1H), 4.75 (m, 3H), 4.30 (d, J=8.4 Hz, 1H), 4.19 (m, 4H), 3.86 (d, J=6.8 Hz, 1H), 3.67 (m, 3H), 3.50 (m, 1H), 2.78 (m, 1H), 2.40 (s, 3H), 2.28 (m, 2H), 2.17 (s, 3H), 2.00 (s, 3H), 1.92 (m, 1H), 1.73 (s, 3H), 1.71 (s, 1H), 1.62 (s, 1H), 1.29 (t, J=6.9 Hz, 3H), 1.18 (s, 6H), 1.16 (d, J=6.3 Hz, 3H), 1.12 (d, J=6.3 Hz, 3H).

$^{13}$C NMR (CDCl$_3$, 75.5 Hz) δ 202.1, 169.9, 169.5, 167.5, 167.0, 153.9, 149.9, 142.7, 140.8, 133.6, 133.1, 130.2, 129.1, 128.7, 110.7, 107.7, 97.0, 84.2, 81.0, 79.5, 78.8, 75.2, 75.0, 74.7, 71.8, 70.0, 69.3, 65.2, 61.8, 57.2, 50.0, 46.9, 43.2, 35.1, 26.4, 22.6, 21.9, 21.8, 21.3, 20.9, 14.5, 14.1, 10.7.

EXAMPLE 17
3'-N-Debenzoyl-3'-desphenyl-3'-N-(isopropyloxycarbonyl)-3'-(2-furyl)-7-O-[(2-hydroxyethoxy)methyl]paclitaxel HRFABMS (NOBA) M+H calcd for $C_{45}H_{58}NO_{18}$ 900.3654. Found: 900.3640.

IR (film) 3440, 1722, 1242 cm$^{-1}$ $^1$H NMR (CDCl$_3$, 300 MHz) δ 8.07 (d, J=7.2 Hz, 2H), 7.56 (t, J=7.5 Hz, 1H), 7.46 (t, J=7.8 Hz, 2H), 7.39 (s, 1H), 6.37 (s, 1H), 6.35 (m, 1H), 6.31 (m, 1H), 6.18 (t, J=7.8 Hz, 1H), 5.65 (d, J=6.9 Hz, 1H), 5.38 (m, 2H), 4.90 (d, J=7.8 Hz, 1H), 4.75 (m, 4H), 4.28 (d, J=8.4 Hz, 1H), 4.16 (m, 2H), 3.83 (d, J=6.8 Hz, 1H), 3.66 (m, 3H), 3.50 (m, 2H), 2.77 (m, 1H), 2.37 (s, 3H), 2.29 (m, 2H), 2.18 (s, 3H), 1.91 (s, 4H), 1.75 (m, 2H), 1.72 (s, 4H), 1.20 (s, 3H), 1.18 (s, 3H), 1.16 (d, J=6.3 Hz, 3H), 1.11 (d, J=6.3 Hz, 3H).

$^{13}$C NMR (CDCl$_3$, 75.5 Hz) δ 202.0, 172.3, 170.5, 169.6, 166.9, 155.8, 151.2, 142.5, 140.0, 133.7, 133.5, 130.2, 129.1, 128.7, 110.7, 107.6, 96.7, 84.1, 81.2, 79.2. 78.6, 75.3, 74.6, 72.3, 71.8, 70.0, 69.2, 61.8, 57.3, 52.0, 47.0, 43.3, 35.3, 35.0, 26.5, 22.5, 22.0, 21.9, 21.1, 20.9, 14.6, 10.7.

EXAMPLE 18
3'-N-Debenzoyl-3'-desphenyl-3'-N-(isopropyloxycarbonyl)-3'-(2-furyl)-7-O-[(5-hydroxypentyloxy)methyl]paclitaxel FABMS (NOBA) M+H calcd for $C_{48}H_{64}NO_{18}$ 942.4123. Found: 942.4149.

IR (film) 3442, 1716, 1242, 1110, 1044, 1026 cm$^{-1}$ $^1$H NMR (CDCl$_3$, 300 MHz) δ 8.07 (d, J=7.2 Hz, 2H), 7.57 (t, J=7.5 Hz, 1H), 7.46 (t, J=7.8 Hz, 2H), 7.39 (s, 1H), 6.35 (m, 2H), 6.30 (m, 1H), 6.20 (t, J=8.1 Hz, 1H), 5.64 (d, J=6.9 Hz, 1H), 5.51 (d, J=9.6 Hz, 1H), 5.35 (br d, J=9.3 Hz, 1H), 4.91 (d, J=7.8 Hz, 1H), 4.80 (m, 1H), 4.66 (m, 3H), 4.28 (d, J=8.4 Hz, 1H), 4.10 (m, 2H), 3.83 (d, J=6.8 Hz, 1H), 3.76 (br s, 1H), 3.57 (m, 3H), 3.39 (m, 1H), 2.78 (m, 1H), 2.37 (s, 3H), 2.27 (d, J=9.3 Hz, 2H), 2.18 (s, 3H), 1.92 (s, 3H), 1.88 (m, 2H), 1.82 (s, 1H), 1.65 (s, 3H), 1.56–135 (m, 6H), 1.19 (s, 3H), 1.18 (s, 3H), 1.16 (d, J=6.3 Hz, 3H), 1.12 (d, J=6.3 Hz, 3H).

$^{13}$C NMR (CDCl$_3$, 75.5 Hz) δ 202.1, 170.9, 169.4, 167.0, 155.7, 151.4, 142.5, 140.0, 133.7, 133.5, 130.1, 129.2, 128.6, 110.6 107.5, 96.0, 84.3, 81.4, 78.6, 75.3, 74.6, 72.0, 69.1, 68.2, 62.8, 57.3, 52.0, 47.0, 43.2, 35.3, 34.8, 32.5, 29.5, 26.6, 22.6, 22.5, 22.0, 21.9, 21.0, 20.9, 14.8, 10.7.

EXAMPLE 19
3'-N-Debenzoyl-3'-desphenyl-3'-N-(isopropyloxycarbonyl)-3'-(2-furyl)-7-O-[(6-hydroxyhexyloxy)methyl]paclitaxel HRFABMS (NOBA) M+H calcd for $C_{49}H_{66}NO_{18}$ 956.4280. Found: 956.4309.

IR (film) 3372, 1718, 1244, 1110, 1050, 1024 cm$^{-1}$ $^1$H NMR (CDCl$_3$, 300 MHz) δ 8.05 (d, J=7.2 Hz, 2H), 7.55 (t, J=7.5 Hz, 1H), 7.44 (t, J=7.8 Hz, 2H), 7.37 (s, 1H), 6.33 (m, 2H), 6.29 (m, 1H), 6.15 (t, J=8.2 Hz, 1H), 5.62 (m, 2H), 5.31 (br d, J=9.3 Hz, 1H), 4.90 (d, J=7.8 Hz, 1H), 4.74 (m, 1H), 4.67 (m, 3H), 4.26 (d, J=8.4 Hz, 1H), 4.11 (m, 2H), 3.97 (m, 1H), 3.81 (d, J=6.8 Hz, 1H), 3.56 (t, J=6.6 Hz, 4H), 3.32 (m, 1H), 2.77 (m, 1H), 2.64 (s, 1H), 2.61 (s, 1H), 2.34 (s, 3H), 2.28 (m, 2H), 2.16 (s, 3H), 1.90 (s, 3H), 1.70 (s, 3H), 1.51 (m, 4H), 1.33 (m, 4H), 1.20 (m, 12H).

$^{13}$C NMR (CDCl$_3$, 75.5 Hz) δ 202.1, 177.9, 172.2, 170.5, 169.5, 166.9, 155.8, 151.3, 142.4, 140.1, 133.6, 133.5, 130.1, 129.2, 128.6, 110.6, 107.5, 96.8, 84.3, 81.2, 79.5, 78.4, 76.5, 75.2, 74.6, 72.0, 71.8, 69.1, 68.3, 62.7, 57.3, 52.1, 46.9, 43.3, 35.3, 32.5, 29.9, 26.5, 25.9, 25.5, 22.5, 22.0, 21.9, 21.1, 20.9, 14.6, 9.5.

EXAMPLE 20

3'-N-Debenzoyl-3'-desphenyl-3'-N-(isopropyloxycarbonyl)-3'-(2-furyl)-7-O-[(7-hydroxyheptyloxy)methyl]paclitaxel HRFABMS (NOBA) M+H calcd for C$_{50}$H$_{68}$NO$_{18}$ 970.4436. Found: 970.4424.

IR (film) 3440, 1720, 1242, 1180, 1110, 1050, 1024 cm$^{-1}$ $^1$H NMR (CDCl$_3$, 300 MHz) δ 8.07 (d, J=7.2 Hz, 2H), 7.58 (t, J=7.5 Hz, 1H), 7.46 (t, J=7.8 Hz, 2H), 7.39 (s, 1H), 6.35 (m, 2H), 6.30 (m, 1H), 6.19 (t, J=8.2 Hz, 1H), 5.64 (d, J=6.9 Hz, 1H), 5.38 (m, 2H), 4.92 (d, J=7.8 Hz, 1H), 4.79 (m, 1H), 4.70 (m, 2H), 4.29 (d, J=8.4 Hz, 1H), 4.12 (m, 2H), 3.84 (d, J=6.8 Hz, 1H), 3.58 (m, 4H), 3.33 (m, 1H), 2.80 (m, 1H), 2.36 (s, 3H), 2.29 (d, J=9.3 Hz, 2H), 2.18 (s, 3H), 1.91 (s, 3H), 1.89 (m, 1H), 1.80 (s, 1H), 1.72 (s, 3H), 1.64 (m, 2H), 1.50 (m, 4H), 1.29 (m, 6H), 1.20 (s, 3H), 1.19 (s, 3H), 1.16 (d, J=6.3 Hz, 3H), 1.12 (d, J=6.3 Hz, 3H).

$^{13}$C NMR (CDCl$_3$, 75.5 Hz) δ 202.1, 172.3, 170.4, 169.4, 167.0, 151.3, 142.5, 140.0, 133.7, 133.5, 130.2, 129.2, 128.7, 110.7, 107.6, 96.9, 84.4, 81.2, 79.6, 78.6, 75.2, 74.6, 72.2, 71.8, 69.1, 68.4, 62.9, 57.4, 52.0, 46.9, 43.3, 35.3, 32.6, 29.5, 29.4, 29.0, 26.5, 26.0, 25.6, 22.5, 22.0, 21.9, 21.0, 20.9, 14.7, 10.7.

EXAMPLE 21

3'-N-Debenzoyl-3'-desphenyl-3'-N-(t-butyloxycarbonyl)-3'-(2-methylpropyl)-7-O-methylpaclitaxel Anal. calcd for C$_{44}$H$_{61}$NO$_{15}$; C, 62.61; H, 7.28; N, 1.66. Found: C, 62.44; H, 7.15; N. 1.69.

HRFABMS (NOBA) M+H calcd for C$_{44}$H$_{62}$NO$_{15}$ 844. Found: 844.

IR (KBr) 3528, 1750, 1726, 1248, 1228 cm$^{-1}$ $^1$H NMR (CDCl$_3$, 300 MHz) δ 8.08 (d, J=7.2 Hz, 2H), 7.58 (t, J=7.5 Hz, 1H), 7.46 (t, J=7.8 Hz, 2H), 6.42 (s, 1H), 6.12 (t, J=8.9 Hz, 1H), 5.63 (d, J=6.9 Hz, 1H), 4.96 (d, J=8.1 Hz, 1H), 4.60 (d, J=9.6 Hz, 1H), 4.28 (d, J=8.4 Hz, 1H), 4.15 (m, 3H), 3.86 (m, 2H), 3.32 (s, 3H), 3.28 (m, 1H), 2.72 (m, 1H), 2.36 (m, 4H), 2.19 (s, 3H), 1.95 (s, 3H), 1.70 (m, 6H), 1.34 (s, 3H), 1.30 (s, 9H), 1.19 (s, 6H), 0.95 (m, 6H).

$^{13}$C NMR (CDCl$_3$, 75.5 Hz) δ 202.2, 173.8, 170.1, 169.4, 166.9, 155.5, 140.3, 133.6, 130.2, 129.2, 128.6, 84.1, 81.6, 80.4, 79.7, 76.4, 74.7, 74.6, 73.0, 72.6, 57.5, 57.2, 51.3, 47.2, 41.1, 35.3, 32.3, 28.2, 26.4, 24.7, 23.2, 22.6, 21.9, 20.9, 18.6, 14.7, 10.4.

EXAMPLE 22

3'-Desphenyl-3'-(2-furyl)-7-O-methylpaclitaxel

HRFABMS (NOBA) M+H calcd for C$_{47}$H$_{54}$NO$_{16}$ 888.3443. Found: 888.3432.

IR (KBr) 3450, 1750, 1722, 1712, 1268, 1244, 1024 cm$^{-1}$ $^1$H NMR (CDCl$_3$, 300 MHz) δ 8.09 (d, J=7.2 Hz, 2H), 7.73 (d, J=7.2 Hz, 2H), 7.57 (m, 1H), 7.45 (m, 6H), 6.92 (d, J=9.2 Hz, 1H), 6.38 (s, 2H), 6.33 (s, 1H), 6.18 (t, J=8.1 Hz, 1H), 5.86 (dd, J=9.3, 2.4 Hz, 1H), 5.65 (d, J=6.9 Hz, 1H), 4.91 (d, J=8.4 Hz, 1H), 4.80 (m, 1H), 4.68 (d, J=7.5 Hz, 1H), 4.62 (d, J=7.5 Hz, 1H), 4.29 (d, J=8.4 Hz, 1H), 4.16 (d, J=8.4 Hz, 1H), 4.10 (dd, J=10.5, 3.6 Hz, 1H), 3.84 (d, J=6.9 Hz, 1H), 3.60 (d, J=5.4 Hz, 1H), 3.27 (s, 3H), 2.78 (m, 1H), 2.40 (s, 3H), 2.34 (d, J=8.7 Hz, 2H), 2.18 (s, 3H), 2.00 (m, 1H), 1.89 (s, 3H), 1.80 (s, 1H), 1.75 (s, 3H), 1.18 (s, 6H).

$^{13}$C NMR (CDCl$_3$, 75.5 Hz) δ 202.1, 172.2, 170.4, 169.4, 167.0, 166.9, 150.8, 142.7, 139.9, 133.7, 133.6, 133.4, 132.1, 130.2, 129.2, 128.7, 127.1, 110.8, 108.0, 98.2, 84.3, 81.2, 79.8, 78.5, 75.3, 74.5, 72.3, 71.7, 57.4, 55.8, 50.2, 46.9, 43.2, 35.4, 29.5, 26.6, 22.6, 21.0, 20.9, 14.7, 10.7.

We claim:

1. A compound of the formula (I):

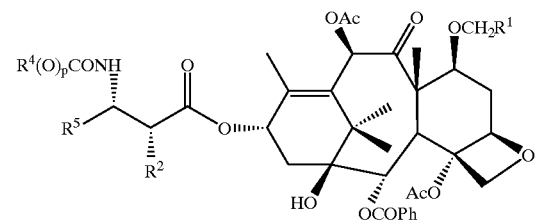

(I)

wherein R$^1$ is hydrogen, C$_{1-8}$ alkyloxy, C$_{2-8}$ alkenyloxy, or C$_{2-8}$ alkynyloxy, each can be optionally substituted with hydroxy; R$^2$ is hydroxy, —OC(O)R$^x$ or —OC(O)OR$^x$; R$^4$ and R$^5$ are independently C$_{1-8}$ alkyl, C$_{2-8}$ alkenyl, C$_{2-8}$ alkynyl, or —Z—R$^6$; p is zero or one; Z is a direct bond, C$_{1-8}$ alkylene or C$_{2-8}$ alkenediyl; R$^6$ is aryl, substituted aryl, C$_{3-8}$ cycloalkyl or heteroaryl; and R$^x$ is C$_{1-8}$ alkyl optionally, substituted with one to six same or different halogen atoms, C$_{3-8}$ cycloalkyl or C$_{2-8}$ alkenyl; or R$^x$ is a radical of the formula

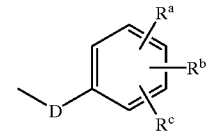

wherein D is a bond or C$_{1-8}$ alkyl; and R$^a$, R$^b$ and R$^c$ are independently hydrogen, amino, C$_{1-8}$ alkylamino, di-C$_{1-8}$alkylamino, halogen, C$_{1-8}$ alkyl, or C$_{1-8}$ alkyloxy.

2. A compound of claim 1 in which R$^1$ is hydrogen or C$_{1-8}$ alkyloxy optionally substituted with hydroxy; R$^2$ is hydroxy or —OC(O)OR$^x$; R$^4$ and R$^5$ are independently C$_{1-8}$ alkyl, C$_{2-8}$ alkenyl, or —Z—R$^6$ in which Z is a direct bond; R$^6$ is aryl, furyl or thienyl; and R$^x$ is C$_{1-8}$ alkyl.

3. The compound of claim 2 that is 7-O-methylpaclitaxel.

4. The compound of claim 2 that is 3'-N-debenzoyl-3'-N-(t-butyloxycarbonyl)-7-O-methoxymethylpaclitaxel.

5. The compound of claim 2 that is 3'-N-debenzoyl-3'-N-(t-butyloxycarbonyl)-7-O-[(2-hydroxyethoxy)methyl]paclitaxel.

6. The compound of claim 2 that is 3'-N-debenzoyl-3'-desphenyl-3'-N-(t-butyloxycarbonyl)-3'-(2-furyl)-7-O-methoxymethylpaclitaxel.

7. The compound of claim 2 that is 3'-N-debenzoyl-3'-desphenyl-3'-N-(t-butyloxycarbonyl)-3'-(2-furyl)-7-O-[(2-hydroxyethoxy)methyl]paclitaxel.

8. The compound of claim 2 that is 2'-O-ethoxycarbonyl-3'-N-debenzoyl-3'-N-(t-butyloxycarbonyl)-7-O-methoxymethylpaclitaxel.

9. The compound of claim 2 that is 2'-O-ethoxycarbonyl-3'-N-debenzoyl-3'-N-(t-butyloxycarbonyl)-7-O-[(2-hydroxyethoxy)methyl]paclitaxel.

10. The compound of claim 2 that is 2'-O-ethoxycarbonyl-3'-N-debenzoyl-3'-desphenyl-3'-N-(t-butyloxycarbonyl)-3'-(2-furyl)-7-O-methylpaclitaxel.

11. The compound of claim 2 that is 2'-O-ethoxycarbonyl-3'-N-debenzoyl-3'-N-(t-butyloxycarbonyl)-7-O-methylpaclitaxel.

12. The compound of claim 2 that is 3'-N-debenzoyl-3'-desphenyl-3'-N-(t-butyloxycarbonyl)-3'-(2-furyl)-7-O-[(4-hydroxybutyloxy)methyl]paclitaxel.

13. The compound of claim 2 that is 3'-N-debenzoyl-3'-desphenyl-3'-N-(t-butyloxycarbonyl)-3'-(2-furyl)-7-O-[(5-hydroxypentyloxy)methyl]paclitaxel.

14. The compound of claim 2 that is 3'-N-debenzoyl-3'-desphenyl-3'-N-(t-butyloxycarbonyl)-3'-(2-furyl)-7-O-[(3-hydroxypropyloxy)methyl]paclitaxel.

15. The compound of claim 2 that is 2'-O-ethoxycarbonyl-3'-N-debenzoyl-3'-desphenyl-3'-N-(t-butyloxycarbonyl)-3'-(2-furyl)-7-O-[(2-hydroxyethoxy)methyl]paclitaxel.

16. The compound of claim 2 that is 2'-O-ethoxycarbonyl-3'-N-debenzoyl-3'-desphenyl-3'-N-(isopropyloxycarbonyl)-3'-(2-furyl)-7-O-[(2-hydroxyethoxy)methyl]paclitaxel.

17. The compound of claim 2 that is 3'-N-debenzoyl-3'-desphenyl-3'-N-(isopropyloxycarbonyl)-3'-(2-furyl)-7-O-[(2-hydroxyethoxy)methyl]paclitaxel.

18. The compound of claim 2 that is 3'-N-debenzoyl-3'-desphenyl-3'-N-(isopropyloxycarbonyl)-3'-(2-furyl)-7-O-[(5-hydroxypentyloxy)methyl]paclitaxel.

19. The compound of claim 2 that is 3'-N-debenzoyl-3'-desphenyl-3'-N-(isopropyloxycarbonyl)-3'-(2-furyl)-7-O-[(6-hydroxyhexyloxy)methyl]paclitaxel.

20. The compound of claim 2 that is 3'-N-debenzoyl-3'-desphenyl-3'-N-(t-butyloxycarbonyl)-3'-(2-methylpropyl)-7-O-methylpaclitaxel.

21. The compound of claim 2 that is 3'-desphenyl-3'-(2-furyl)-7-O-methylpaclitaxel.

22. A pharmaceutical composition which comprises an antitumor effective amount of a compound of claim 1 and a pharmaceutically acceptable carrier.

23. A method for inhibiting tumor growth in a mammalian host which comprises administering to said mammal a tumor-growth inhibiting amount of a compound of claim 1.

* * * * *